(12) United States Patent
Stratton et al.

(10) Patent No.: US 9,254,177 B2
(45) Date of Patent: Feb. 9, 2016

(54) HEAD CLAMP FOR IMAGING AND NEUROSURGERY

(75) Inventors: Mathew David Frederick Stratton, Stroud (GB); Hugo George Derrick, Stroud (GB)

(73) Assignee: RENISHAW (IRELAND) LIMITED, Swords (IE)

( * ) Notice: Subject to any disclaimer, the term of this patent is extended or adjusted under 35 U.S.C. 154(b) by 611 days.

(21) Appl. No.: 13/320,953

(22) PCT Filed: May 20, 2010

(86) PCT No.: PCT/GB2010/001003
§ 371 (c)(1),
(2), (4) Date: Nov. 17, 2011

(87) PCT Pub. No.: WO2010/133839
PCT Pub. Date: Nov. 25, 2010

(65) Prior Publication Data
US 2012/0060847 A1 Mar. 15, 2012

(30) Foreign Application Priority Data
May 21, 2009 (GB) .................................. 0908787.5

(51) Int. Cl.
*A61F 5/00* (2006.01)
*A61F 5/04* (2006.01)
(Continued)

(52) U.S. Cl.
CPC .............. *A61B 19/203* (2013.01); *A61B 17/56* (2013.01); *A61B 17/58* (2013.01); *A61B 17/60* (2013.01);
(Continued)

(58) Field of Classification Search
CPC ............... A61F 5/00; A61F 5/01; A61F 5/04; A61F 5/37; A61F 5/3707; A61B 17/56; A61B 17/58; A61B 17/60; A61B 17/64; A61B 19/203; A61B 2019/467; A61B 2019/5454; A61B 2019/5483; G06F 3/00; G06F 3/01; G06F 3/016; G01D 13/00; G01D 13/22; G01D 13/24
USPC ........ 128/845; 606/53–54, 59, 267, 271, 272, 606/130; 602/32–37; 33/700, 832, 813, 33/815; 235/133 R, 137, 138, 142, 133 A; 251/205, 206–208; 116/4, 205, 291, 116/294, 296
See application file for complete search history.

(56) References Cited

U.S. PATENT DOCUMENTS 4,108,426 A 8/1978 Lindstroem et al.
4,169,478 A 10/1979 Hickmann
(Continued)

FOREIGN PATENT DOCUMENTS

DE 20 2004 006 726 U1 6/2004
DE 203 16 926 U1 8/2004
(Continued)

OTHER PUBLICATIONS

Dec. 28, 2012 Office Action issued in U.S. Appl. No. 13/320,942.
(Continued)

*Primary Examiner* — Alireza Nia
*Assistant Examiner* — Brandon L Jackson
(74) *Attorney, Agent, or Firm* — Oliff PLC

(57) ABSTRACT

A head clamp for neurosurgery is described that includes a member for at least partially encircling the head of a subject. The first end and second end of the head clamp include first and second skull attachment portions for attaching the member to the head of a subject. A position setter, such as an indexing mechanism, is also provided that allows the member to be moved or indexed between at least two repeatable relative positions.

16 Claims, 16 Drawing Sheets

Figure 1:
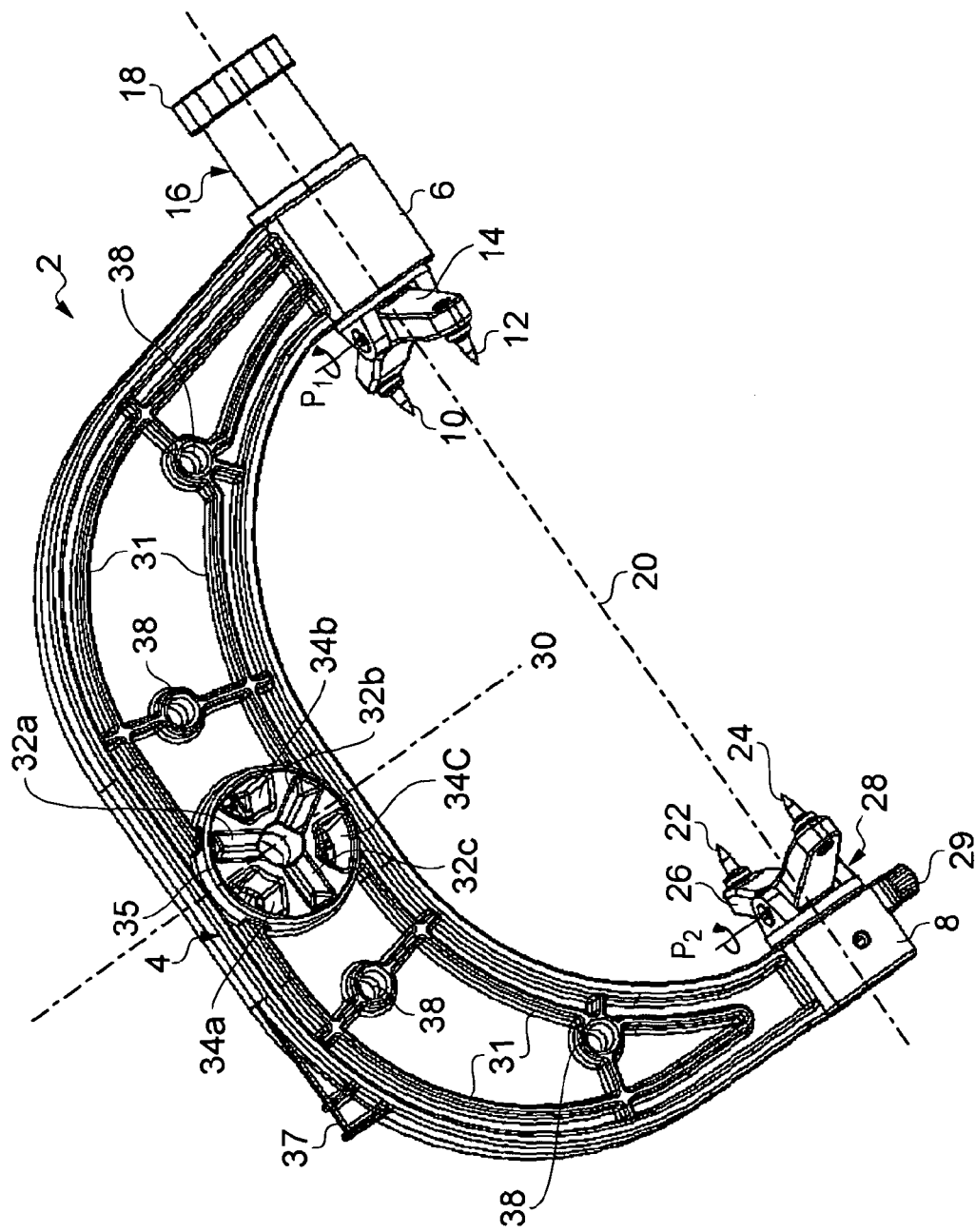

(51) Int. Cl.

| | | |
|---|---|---|
| *A61B 17/00* | (2006.01) | |
| *A61B 17/56* | (2006.01) | |
| *A61B 19/00* | (2006.01) | |
| *A61B 17/70* | (2006.01) | |
| *A61G 15/00* | (2006.01) | |
| *G08B 7/00* | (2006.01) | |
| *G01D 13/22* | (2006.01) | |
| *G01D 11/06* | (2006.01) | |
| *G01D 11/16* | (2006.01) | |
| *G01D 13/24* | (2006.01) | |
| *A61F 4/00* | (2006.01) | |
| *A61B 17/58* | (2006.01) | |
| *A61B 17/64* | (2006.01) | |
| *A61F 5/37* | (2006.01) | |
| *A61F 5/01* | (2006.01) | |
| *A61B 17/60* | (2006.01) | |
| *G06F 3/01* | (2006.01) | |
| *G06F 3/00* | (2006.01) | |

(52) U.S. Cl.
CPC ............ *A61B 17/64* (2013.01); *A61B 17/6433* (2013.01); *A61B 17/6458* (2013.01); *A61B 2019/467* (2013.01); *A61B 2019/5454* (2013.01); *A61B 2019/5483* (2013.01); *A61F 5/00* (2013.01); *A61F 5/01* (2013.01); *A61F 5/37* (2013.01); *A61F 5/3707* (2013.01); *G01D 13/22* (2013.01); *G01D 13/24* (2013.01); *G06F 3/00* (2013.01); *G06F 3/01* (2013.01); *G06F 3/016* (2013.01)

(56) References Cited

U.S. PATENT DOCUMENTS

| | | | |
|---|---|---|---|
| 4,350,159 A | 9/1982 | Gouda | |
| 5,040,547 A | 8/1991 | Bergström | |
| 5,254,079 A | 10/1993 | Agbodoe et al. | |
| 5,281,232 A | 1/1994 | Hamilton et al. | |
| 5,318,509 A | 6/1994 | Agbodoe | |
| 5,423,832 A | 6/1995 | Gildenberg | |
| 5,474,564 A | 12/1995 | Clayman et al. | |
| 5,537,704 A | 7/1996 | Dinkler | |
| 5,569,175 A * | 10/1996 | Chitwood | 602/32 |
| 5,706,811 A | 1/1998 | Takeda et al. | |
| 5,830,162 A * | 11/1998 | Giovannetti | 601/23 |
| 5,855,582 A | 1/1999 | Gildenberg | |
| 5,947,981 A | 9/1999 | Cosman | |
| 6,045,553 A | 4/2000 | Iversen et al. | |
| 6,071,288 A | 6/2000 | Carol et al. | |
| 6,080,164 A | 6/2000 | Oshio et al. | |
| 6,117,143 A | 9/2000 | Hynes et al. | |
| 6,179,846 B1 | 1/2001 | McFadden | |
| 6,198,961 B1 | 3/2001 | Stern et al. | |
| 6,259,943 B1 | 7/2001 | Cosman et al. | |
| 6,381,783 B2 | 5/2002 | Reinhardt et al. | |
| 6,540,707 B1 * | 4/2003 | Stark et al. | 602/13 |
| 6,599,257 B2 * | 7/2003 | Al-Obaidi et al. | 601/5 |
| 6,629,982 B2 | 10/2003 | Day et al. | |
| 7,229,451 B2 | 6/2007 | Day et al. | |
| 7,231,723 B1 | 6/2007 | O'Neill et al. | |
| 2001/0029379 A1 | 10/2001 | Grotehuis et al. | |
| 2001/0039422 A1 | 11/2001 | Carol et al. | |
| 2001/0052151 A1 | 12/2001 | Reinhardt et al. | |
| 2002/0151907 A1 | 10/2002 | Day et al. | |
| 2003/0199886 A1 | 10/2003 | Thomas | |
| 2004/0260311 A1 | 12/2004 | Bourel et al. | |
| 2006/0009787 A1 | 1/2006 | Tai | |
| 2006/0052792 A1 | 3/2006 | Boettiger et al. | |
| 2007/0250071 A1 | 10/2007 | Soerensen et al. | |
| 2008/0269777 A1 | 10/2008 | Appenrodt et al. | |
| 2009/0079431 A1 | 3/2009 | Piferi et al. | |

FOREIGN PATENT DOCUMENTS

| | | |
|---|---|---|
| EP | 1 026 513 A2 | 8/2000 |
| EP | 1 112 034 B1 | 4/2004 |
| EP | 1 510 182 A2 | 3/2005 |
| EP | 1 849 427 A1 | 10/2007 |
| GB | 2 370 778 A | 7/2002 |
| JP | A-11-137568 | 5/1999 |
| JP | A-2008-194144 | 8/2008 |
| WO | WO 99/11176 | 3/1999 |
| WO | WO 01/76481 A2 | 10/2001 |
| WO | WO 2004/058085 A1 | 7/2004 |
| WO | WO 2006/118510 A1 | 11/2006 |
| WO | WO 2006/134357 A1 | 12/2006 |
| WO | WO 2007/040507 A2 | 4/2007 |
| WO | WO 2007/044469 A2 | 4/2007 |
| WO | WO 2009/040677 A2 | 4/2009 |
| WO | WO 2010/133838 A1 | 11/2010 |
| WO | WO 2010/133839 A1 | 11/2010 |
| WO | WO 2010/133847 A1 | 11/2010 |

OTHER PUBLICATIONS

Oct. 20, 2009 Search Report issued in Great Britain Patent Application No. GB0908787.5.

Sep. 2, 2010 International Search Report issued in International Application No. PCT/GB2010/001003.

Sep. 2, 2010 Written Opinion of the International Searching Authority issued in International Application No. PCT/GB2010/001003.

Oct. 20, 2009 Search Report issued in Great Britain Patent Application No. GB0908785.9.

Sep. 9, 2010 International Search Report issued in International Application No. PCT/GB2010/001002.

Oct. 20, 2009 Search Report issued in Great Britain Patent Application No. GB0908784.2.

Aug. 24, 2010 International Search Report issued in International Application No. PCT/GB2010/001013.

Aug. 24, 2010 Written Opinion of the International Searching Authority issued in International Application No. PCT/GB2010/001013.

U.S. Appl. No. 13/320,942 in the name of Stratton et al., filed Nov. 17, 2011.

* cited by examiner

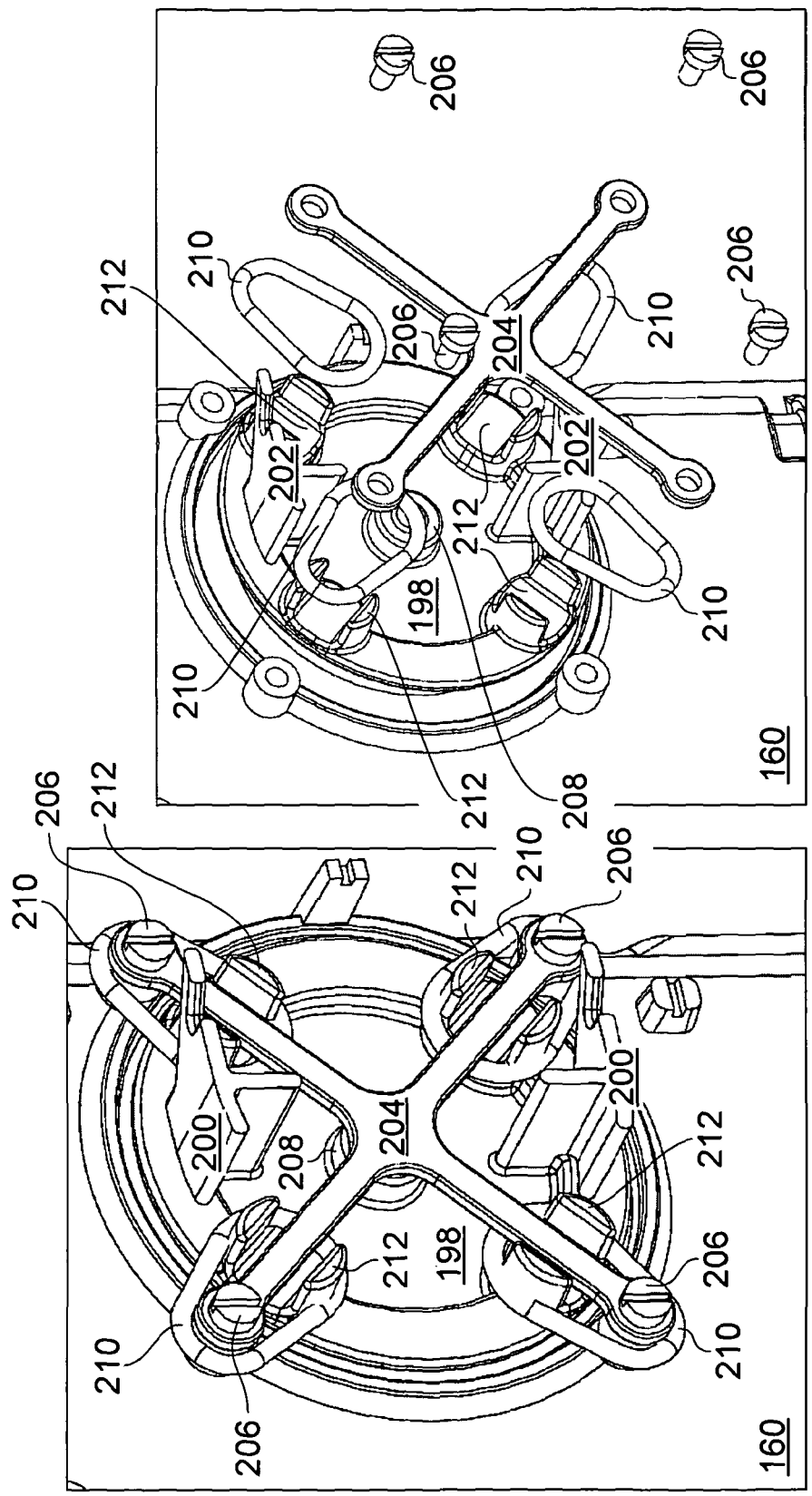

HEAD CLAMP FOR IMAGING AND NEUROSURGERY

The present invention relates to a clamp for attachment to the head of a subject, and in particular to an indexable head clamp suitable for use in both magnetic resonance imaging (MRI) of the head and stereotactic neurosurgery procedures.

It is known to provide various types of head clamp to grip and stabilise the head of a subject during neurosurgical procedures. One known type of head clamp comprises a generally c-shaped frame member for partially encircling the head of a subject with a pin or pins provided at each end of the frame member to engage the skull. Such head clamps are placed in the desired position relative to the head before being firmly attached in place. Once attached, the head clamp can be secured to an operating table. Various examples of such head clamps are described in U.S. Pat. No. 4,169,478, U.S. Pat. No. 5,318,509, U.S. Pat. No. 6,381,783 and U.S. Pat. No. 7,229,451.

In stereotactic neurosurgery, a neurosurgeon will often have to insert instruments into the brain with millimeter accuracy. In particular, the success of stereotactic neurosurgery is highly dependent on the accuracy with which neurosurgical instruments, such as electrodes or catheters, can be guided to a predetermined target site within the brain. Stereotactic head frames for use in precision guided neurosurgery are known. For example, the Leksell (Registered Trade mark) frame produced by Elekta AB, Sweden includes a base ring attachable to the base of the skull. Once the base ring is attached to the subject's head and has been imaged it acts as a platform of known position relative to the head from which instruments can be stereotactically guided to the required target site or sites in the brain. The base ring can also be locked to an operating table to immobilise the head. It has also been proposed previously to mount MRI coils directly to the base ring of a Leksell type frame. For example, WO2006/134357 describes apparatus in which RF coils for MRI can be directly attached to such a base ring.

According to a first aspect of the present invention, a head clamp for neurosurgery is provided that comprises a member for at least partially encircling the head of a subject, and at least first and second skull attachment portions for attaching the member to the head of a subject, characterised in that the head clamp comprises a position setter that allows the member to be moved between at least two repeatable relative positions.

The present invention thus provides a head clamp for neurosurgery comprising a member that is attachable to a head using first and second skull attachment portions that engage the skull of a subject. The member may be of any shape but it is preferred that the member comprises a c-shaped member. Advantageously, such a c-shaped member partially encircles the head. It should be noted that the term c-shaped member is used herein to encompass members that may be v-shaped, u-shaped, G-shaped, arced, bent or a variant shape thereof. Conveniently, the first and second skull attachment portions are located at the first and second ends of the c-shaped member. Advantageously, the first and second skull attachment portions are locatable at substantially opposite sides of a skull. As described in more detail below, the skull attachment portions may include one or more bone pins or screws that can be secured directly to the skull bone of a subject. A force applicator may also be provided, e.g. as described below, to force such pins into contact with the skull. Means may also be provided to prevent rotation of the first and/or second skull attachment portions relative to the member during the attachment or removal of the head clamp.

The present invention also includes a position setter that allows the member to be moved between at least two repeatable relative positions. The position setter may comprise a position encoder (e.g. a rotary encoder) or positional markings that measure, or allow to be measured, an angle between the member and a part of the head clamp that has an invariant position relative to the skull to which it is attached. Advantageously, the position setter comprises an indexing mechanism that allows, when the head clamp is attached to a head, the member to be indexed between two or more repeatable relative positions.

Providing a head clamp with a position setter in accordance with the present invention allows the member to be moved between at least two repeatable positions that have a known (predetermined) position relative to each other. This allows, for example, measurements (e.g. MRI images) of the head that are tied to a unique reference or datum position on the member when that member is in a first position to be linked back to that reference position when the member has been moved into the second position. In this manner, MRI images of the brain acquired with the member in a first position can be used, after applying appropriate coordinate transformations, to precisely guide neurosurgical devices even when the member has been moved into another position. This ability to move the member into a plurality of repeatable relative positions is particularly advantageous because it enables the member to be moved between different positions that allow optimised imaging (e.g. using MRI) or provide the necessary access to the head for the insertion of neurosurgery devices or instruments. Advantageously, the position setter allows the member to be moved whilst the clamping force for holding the head clamp on the head is applied.

None of the known head clamp arrangements mentioned above provide a position setter according to the present invention. The c-shaped members of known head clamps can be finely adjusted during attachment to the head, but are not moveable between two or more repeatable relative positions. Such known head clamps are simply adjusted into a preferred position and then used as a means for securing the head to an operating table during neurosurgery. Similarly, the base ring of a Leksell frame is secured in position and then used as a reference platform after being imaged; the base ring is therefore specifically designed to be as immobile as possible after attachment to the skull. In contrast to these prior art devices, the present invention offers, by virtue of the provision of a position setter such as an indexing mechanism, the ability to optimise the position of the member relative to the head for different applications without loosing the ability to then use any positional information that has been obtained using the member as a reference or base position.

Advantageously, the member can, when the head clamp is attached to the head of a subject, be moved (e.g. indexed) into a first position. Conveniently, the first position comprises a position in which the member substantially extends around the top of the head (e.g. in a so-called sagittal position) thereby allowing imaging (e.g. MRI) of the head. In such a first position, MRI coils and/or MRI visible fiducial markers may be attached (directly or indirectly) to the member. Orientating the member so that it substantially extends around the top of the head allows such fiducial markers and associated RF coils to be placed in close proximity to the side of the head and allows such coils to extend along the whole side of the head thereby allowing more of the head to be imaged. In other words, the first position of the member may be selected to optimise imaging.

Preferably, the member can, when attached to the head of a subject, be moved (e.g. indexed) into a second position.

Advantageously, the second position comprises a position in which the member substantially extends around a side of the head thereby enabling neurosurgical procedures (e.g. stereotactic neurosurgery) to be performed on the head. Such a second position thus allows the member to be moved away from the top of the head to one side of the head. This allows the surgeon to have improved access, substantially unhindered by the head clamp, to the required part of the head through which the brain will be accessed. In other words, the second position of the member may be selected to optimise access for neurosurgery.

The first and second positions into which the member can be moved are repeatable, relative positions. In other words, the relative difference or change in position of the member between the first and second positions is known. For example, the head clamp may be designed such that there is a certain positional difference between the first and second positions and/or any positional difference may be measured. Knowing the relative difference in the first and second positions means that any position measurements made relative to the member with the head clamp in the first position (e.g. using MRI) can be tied to positions on that member with the head clamp in the second position. In this manner, neurosurgical instruments guided by a stereoguide attached to the member of the head clamp may be accurately guided to target sites in the brain identified using MRI, even though the member may be indexed into different positions during imaging and surgery.

The head clamp may be attached to a skull by only the first and second skull attachment portions. Alternatively, the head clamp may include further skull attachment portions. Advantageously, the first and second skull attachment portions are locatable on substantially opposite sides of a head. Preferably, the first and second skull attachment portions exert a clamping force on the head substantially along a clamping axis. The head clamp, when attached to the head, is conveniently arranged so that the clamping axis is substantially parallel to the anterior commisure posterior commisure (ACPC) plane of the brain. Alignment with the ACPC, which is an internal landmark of the brain, may be achieved sufficiently accurately by aligning the clamping axis with external landmarks such as the cantho-meatal plane. The first skull attachment portion is, in use, conveniently attached to the forehead of the subject.

The member (e.g. a c-shaped member) is advantageously rotatable about the clamping axis. For example, the member may be moveable (e.g. indexable) between two or more rotary positions. The member may thus adopt a first position in which the member substantially extends around the top of the head; this may be defined as a 0° position. A second position in which in which the member substantially extends around a side of the head may then be defined as a +90° or a −90° position (depending on which side of the head it is positioned). Preferably, a plurality of repeatable positions between −135° and 135° are provided. The position setter may, of course, provide other repeatable relative angular positions if required.

In order to provide the positional link between different positions, it is preferable that the user is able to unambiguously establish the particular repeatable relative position into which the member has been placed. This may be achieved by providing markings or the like on the head clamp that allows the selected position to readily determined. If an indexing mechanism is provided, it is also preferred that the member can only be indexed into relatively few different positions thereby ensuring there is no confusion over the position in which the member is located. Preferably, such an indexing mechanism allows the member to be indexed in to fewer than twenty, more preferably fewer than ten, more preferably fewer than five, or more preferably three or fewer, or more preferably fewer than three different repeatable relative positions. If the member is rotatable about an axis as described above, it is preferred that the repeatable relative positions are separated by an angle of at least 5°, more preferably at least 10°, more preferably at least 20°, more preferably at least 45° and more preferably at least 75°.

The position setter may comprise an indexing mechanism of any suitable type. Conveniently, the indexing mechanism allows the member to be indexed when the clamping force for engaging the head clamp with the skull (e.g. as produced by the force applicator) is being applied. Preferably, each indexed position provided by such an indexing mechanism can be selected with no, or negligible, backlash. Advantageously, the indexing mechanism comprises first and second mating parts that may adopt a plurality of different, repeatable, indexed positions relative to one another. The indexing mechanism may comprise parts that provide a v-tooth, Curvic or Hirth coupling. Alternatively, the first part may comprise a plurality of pins that mate with a plurality of tapered holes provided in the second part. In a further alternative embodiment, each part may comprise a set of balls arranged to engage each other to define the plurality of indexed positions. Each indexed position may be provided by a kinematic connection. Advantageously, the first mating part of the indexing mechanism may be rotatable relative to a second mating part of that mechanism; e.g. the first mating part may be located at least partially within the second mating part. A locking screw may be provided to lock the first and second parts into the selected indexed position. The locking screw may engage a feature of the first part or second part.

The first and second skull attachment portions may include any suitable elements for engaging the head. Advantageously, any such elements pass through openings in the skin and directly engage with the skull bone of the subject. The first skull attachment portion and/or the second skull attachment portion may conveniently comprise one or more pins for direct engagement with the skull bone of a subject. Advantageously, the first skull attachment portion comprises the same number of pins as the second skull attachment portion. Preferably, the first and second skull attachment portions each include two pins for direct engagement with the skull bone of a subject. Such an arrangement, in particular providing the first and second skull attachment portions with the same number of pins, is preferred as it allows the member to be loaded with the required clamping force without being substantially distorted or twisted.

Advantageously, each pin has an outer, soft, coating. For example, metal (e.g. titanium) pins may be provided that are coated with an outer layer of soft material (e.g. rubber, plastic etc). Such a coating provides protection against damage to soft tissue during attachment of the head clamp to a subject. It should be noted that a bone attachment pin of this type may also be used in different applications. A pin is thus described herein that comprises a core (e.g. a metal or ceramic core) with a sharp tip, wherein a soft coating is provided on the tip.

The first skull attachment portion may conveniently comprise a pin carrying member that is pivotally attached to the member. For example, the pin carrying member may be pivotally attached to the first end of a c-shaped member. The second skull attachment portion may also comprise a pin carrying member that is pivotally attached to the member. For example, the pin carrying member may be pivotally attached to the second end of a c-shaped member. Each pin carrying member may carry, or be arranged to carry, one or more pins for direct engagement with the skull bone of a subject. Attaching pins to the end of the c-shaped member using such a pivotally attached pin carrying member allows the applied clamping force to be evenly distributed between the pins and minimises out of plane distortions of the member. Advantageously, each pin carrying member is arranged to pivot relative to the member in a single plane.

The head clamp may comprise a force applicator to urge the first and second skull attachment portions into engagement with the skull. The force applicator may urge the first and second skull attachment portions into engagement with the skull with a variable, e.g. user definable, force. Preferably, the force applicator urges the first and second skull attachment portions into engagement with the skull with a predetermined amount of force. For example, the force applicator may be arranged to apply a certain force (e.g. 200 N) to the skull per skull attachment pin. Advantageously, the force applicator may include a force indicator for indicating when a preferred engagement force has been applied. The force indicator preferably comprises a tactile indicator, such as a recessed rod that becomes flush with a reference surface when the required force is applied. The force applicator may also comprise a force limiter for ensuring that a certain force limit is not exceeded. For example, the force limiter may ensure the predetermined amount of force is not exceeded.

The force applicator may be located adjacent to only one of the first and second skull attachment portions. For example, the force applicator may be located at only one end of a c-shaped member (e.g. at the opposite end to the position setter or indexing mechanism). This, however, obviously results in the application of an equal and opposite force at the first and second ends of the c-shaped member. It can also be seen that the clamping force is transmitted between the skull attachment portions via the member. Applying a predetermined clamping force in this manner also ensures that the member is, in use, subjected to the same (predetermined) force and hence deforms, at least approximately, by a known amount. The member does not, therefore, have to be sufficiently rigid to be undistorted by the clamping force. Instead, it is preferred that the member deforms by at least approximately the same amount when the predetermined clamping force is transmitted through it.

The member preferably comprises at least one datum feature. Each such datum feature preferably provides a positional reference point on or in a fixed positional relationship to the member. Each datum feature may be a marking (e.g. a visible or MRI visible marking) or a physical feature or set of features. A single datum feature may be provided. Advantageously, a datum feature is provided on each side (e.g. on opposing faces) of the member.

Advantageously, the at least one datum feature is located substantially on a neutral axis of distortion of the member; the neutral axis being an axis about which the member deforms when the clamping force is applied. If two datum features are provided on opposite sides or faces of the member, each datum feature may be located substantially on a neutral axis of distortion of the member. Any variations in the applied clamping force will thus have no substantial effect on the position of the datum feature(s) relative to the first and second skull attachment portions or the head to which the clamp is attached. Associated apparatus may then include a feature that is complementary to the datum feature such that the associated apparatus may be repeatedly placed in the same defined position relative to the datum feature of the head clamp.

Advantageously, a datum feature is provided on the member that comprises the first part of a kinematic joint. In other words, the datum feature may comprise a kinematic datum feature. A kinematic datum feature may thus be arranged so that it uniquely constrains an associated, complementary, kinematic feature in each of the 6 degrees of freedom. For example, the datum feature may comprise three v-grooves radially spaced apart from one another by 120° and extending along directions that intersect at a common point. In such an example, the common point may be located substantially on the neutral axis of the member. Associated apparatus (e.g. stereoguides, fiducial markers for MRI etc) may then comprise the second part of the kinematic joint, such as three balls (or at least partly spherical features) spaced in a circle and separated from each other by 120°. The first and second parts of the kinematic joint may, then be arranged to provide a highly repeatable kinematic link in which there is only one constraint on each degree of freedom of movement between the first and second parts.

Advantageously, the head clamp comprises at least one attachment feature that allows the head clamp to be secured to associated apparatus. Preferably, the at least one attachment feature is located substantially on a neutral axis of distortion of the c-shaped member. The at least one attachment feature may thus provide a mechanical linkage by which the head clamp can be secured to associated apparatus such as an operating table bed or an MRI headcoil assembly. A common feature may provide both a datum feature and an attachment feature. Advantageously, the attachment feature is separate from the datum feature. Preferably, a datum feature of the head clamp is accessible when the attachment feature is secured to the associated apparatus. This allows, for example, the at least one attachment feature to be used to secure the head clamp to an operating table bed whilst a feature of a stereoguide is mated with the datum feature of the head clamp. Supplementary attachment features may also be provided on the member if required.

Advantageously, the head clamp is substantially MRI compatible. For example, the member may be formed from a polymer, a reinforced plastic, a filled ceramic or a glass-filled polymer. The head clamp may also include ceramic and/or plastic components. The head clamp may contain some metal components (e.g. springs), but the amount of metal is preferably not enough to cause the generation of eddy currents that are sufficient to cause substantial heating of the structure or induce magnetic field distortions that effect the MR image.

The present invention also provides a head clamping kit that comprises a head clamp as described above and a secondary clamping device that is attachable to the head clamp. Advantageously, the secondary clamping device provides, when attached to the head clamp, additional mechanical support to the member. Conveniently, the secondary clamping device provides such mechanical support to the member only in the event of mechanical failure of that member. In other words, the secondary clamp is normally non-load bearing and only provides mechanical support if the member fails. This backup or support clamp may be used during surgical procedures in which the force exerted on the head clamp may momentarily exceed safe tolerances.

Also described herein is a kit comprising a head clamp for neurosurgery and a secondary clamping device attachable to the head clamp. The head clamp may comprise a member for at least partially encircling the head of a subject. For example, the head clamp may comprise a c-shaped member for partially encircling the head of a subject. The head clamp may include first and second skull attachment portions; for example provided at the first and second ends of a c-shaped member. The secondary clamping device provides, when attached to the head clamp, additional mechanical support to the member (e.g. the c-shaped member) in the event of mechanical failure of that member.

The present invention also extends to apparatus for imaging the head of a subject that comprises a head clamp as described above and apparatus (e.g. MRI or CT apparatus) for imaging a head. Preferably, the head clamp is releasably attachable to the apparatus. For example, the MRI apparatus may include a clamping mechanism for engaging an attachment feature of the head clamp and/or one or more fiducial markers that can be repeatably attached to a datum feature of the head clamp.

The apparatus for imaging the head of a subject may comprise a housing for at least partially surrounding a body part, and a first fiducial marker assembly retained at least partially within the housing that comprises one or more fiducial markers and a datum feature, the position of the datum feature being fixed relative to the one or more fiducial markers, wherein the first fiducial marker assembly is moveable with respect to the housing and the datum feature is accessible from outside of the housing. Such apparatus may include one or more RF coils for magnetic resonance imaging that are located within the housing. The housing may comprise a first housing part and a second housing part, wherein the first and second housing parts can be moved, e.g. pivoted, into a closed position that defines an imaging space in which a human head can be located. Fiducial marker assemblies may also be provided in each housing part. Such apparatus is described in more detail in Applicant's co-pending PCT patent application, the contents of which are hereby incorporated by reference, that has the same filing date as the present application and claims priority from UK patent application No. 0908784.

The present invention also extends to apparatus for neurosurgery, comprising a head clamp as described above and a stereoguide device for retaining and guiding neurosurgical instruments. Preferably, the stereoguide device is releasably attachable to the head clamp. For example, the neurosurgery apparatus may comprise a clamp for engaging an attachment feature of the head clamp and/or the stereoguide device may be repeatably attached to a datum feature of the head clamp. The member of the head clamp may be moveable into repeatable relative positions that provide an axis of movement or rotation of the stereoguide.

According to a second aspect of the invention, a method of performing neurosurgery is provided that comprises the steps of; (i) attaching an head clamp comprising a moveable member to the head of a subject, (ii) moving the member into a first position and acquiring at least one image of the head, (iii) moving the member into a second position and performing a neurosurgical procedure, wherein the relative difference in position between the first position and the second position of the member is known.

Preferably, the head clamp comprises an indexable member and steps (ii) and (iii) comprise indexing the member into the first position and second position respectively. Advantageously, at least one datum feature is provided on the head clamp that allows images acquired during step (ii) to be related to neurosurgical procedures conducted during step (iii). Preferably, step (i) comprises attaching the head clamp to the head with a predetermined engagement force such that deformations of the member are known. Conveniently, step (i) comprises applying a clamping force substantially along a clamping axis, wherein the clamping axis is aligned, at least approximately, with the cantho-meatal plane of the subject.

Preferably, the member of the head clamp comprises a c-shaped member, wherein the first position of step (ii) is a position in which the c-shaped member substantially extends around the top of the head thereby allowing imaging of the head and the second position of step (iii) is a position in which the c-shaped member substantially extends around a side of the head thereby providing access the head to allow the neurosurgical procedure to be performed.

Also described herein is a head clamp for neurosurgery, comprising; a c-shaped member for partially encircling the head of a subject, and first and second skull attachment portions provided at first and second ends of the c-shaped member, wherein the head clamp comprises at least one fiducial marker (e.g. at least one MRI visible fiducial marker). At least one fiducial marker may be formed integrally with the head clamp. For example, a fiducial marker may form part of, or be fixed to, any part of the head clamp. At least one fiducial marker may be attachable (e.g. releasably attachable) to a part of the head clamp in a known position relative to that part of the head clamp. The head clamp may also comprise a datum feature (e.g. provided on the c-shaped member) that allows associated apparatus to be located in a known position relative to the head clamp. Such a datum feature may also allow the fiducial marker to be attached to the head clamp in a known relative position.

A fiducial assembly may also be provided that comprises at least one fiducial marker (e.g. at least one MRI visible fiducial marker) and a datum feature having a fixed position relative to the at least one fiducial marker. The datum feature may be combined with one or more fiducial markers. The datum feature preferably allow associated apparatus to be located in a known position relative to the assembly. The fiducial assembly may include means for attachment to the skull of a subject. For example, such means may comprise a clamp (e.g. a c-clamp) for securing the fiducial assembly to a skull.

Figure 2:
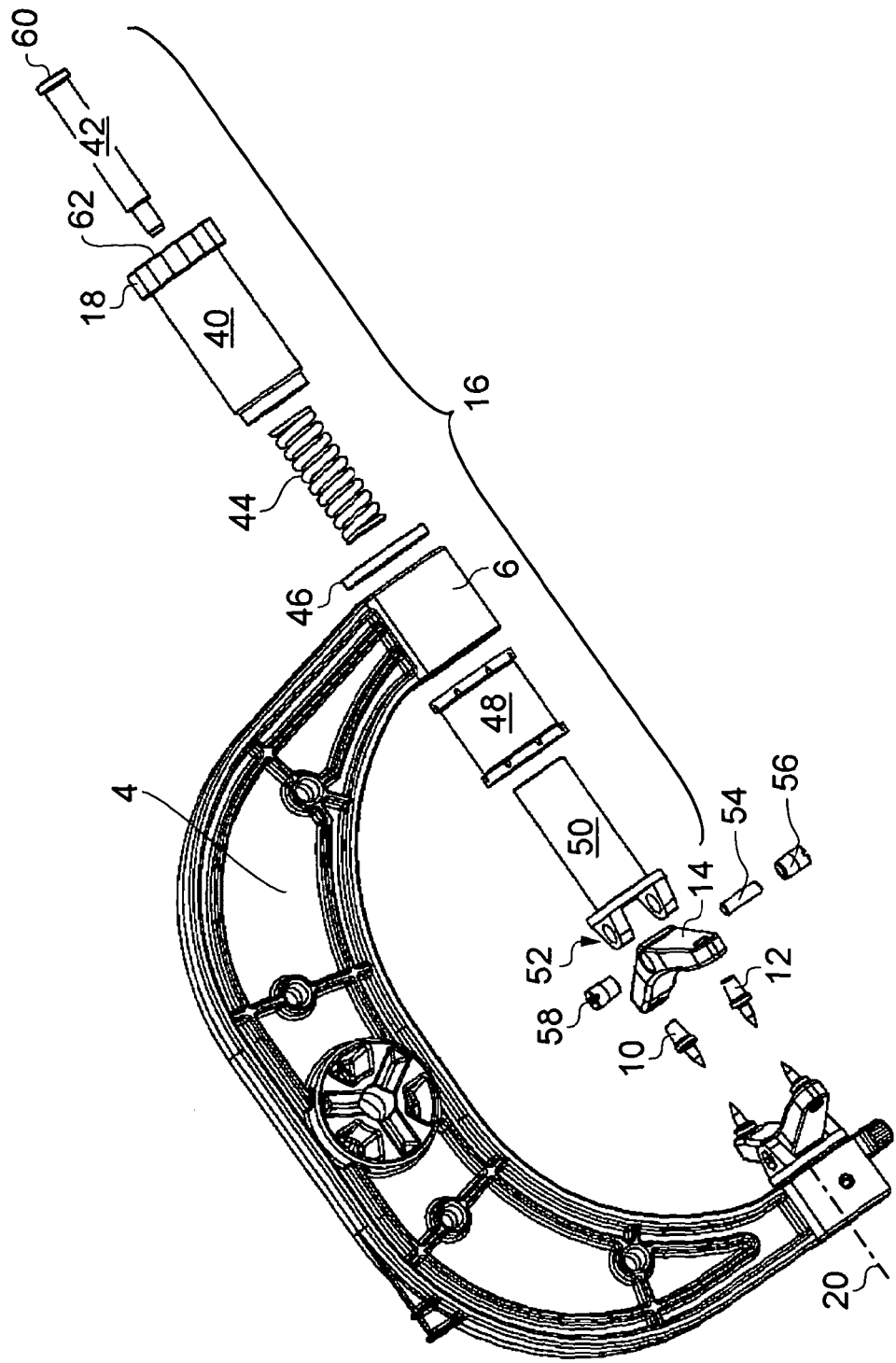
Figure 4:
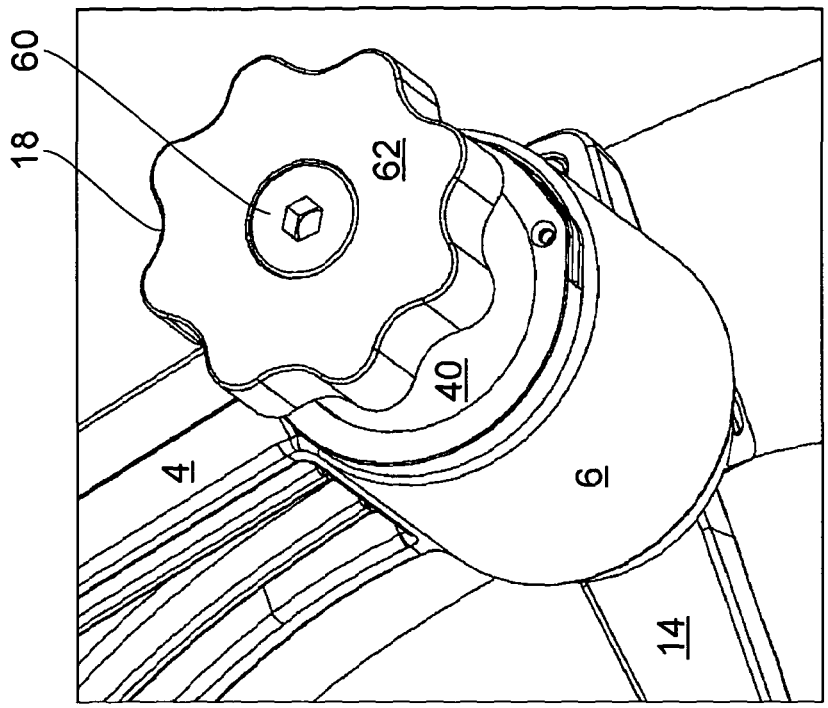
Figure 3:
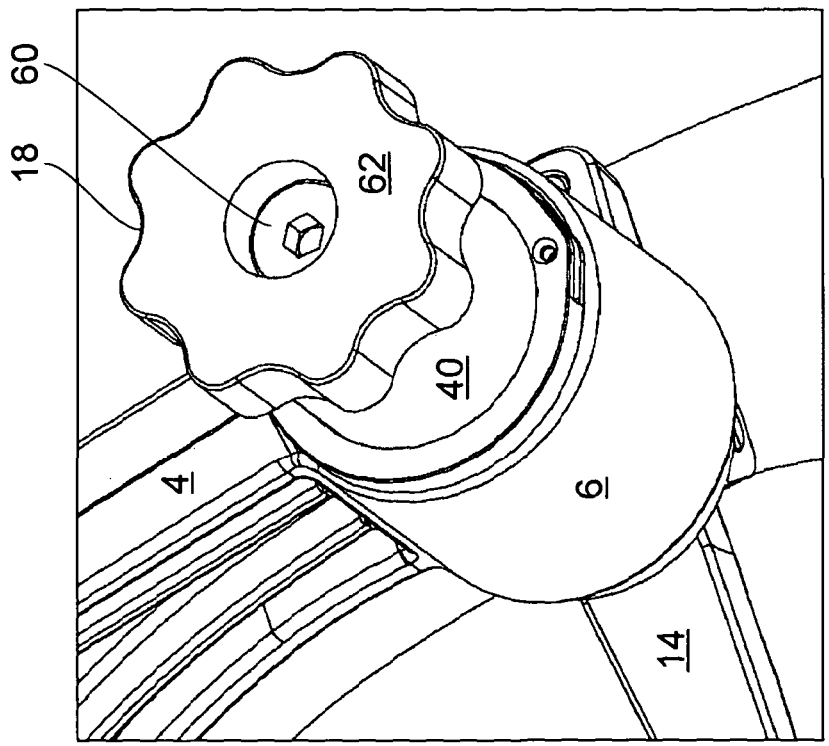
Figure 5:
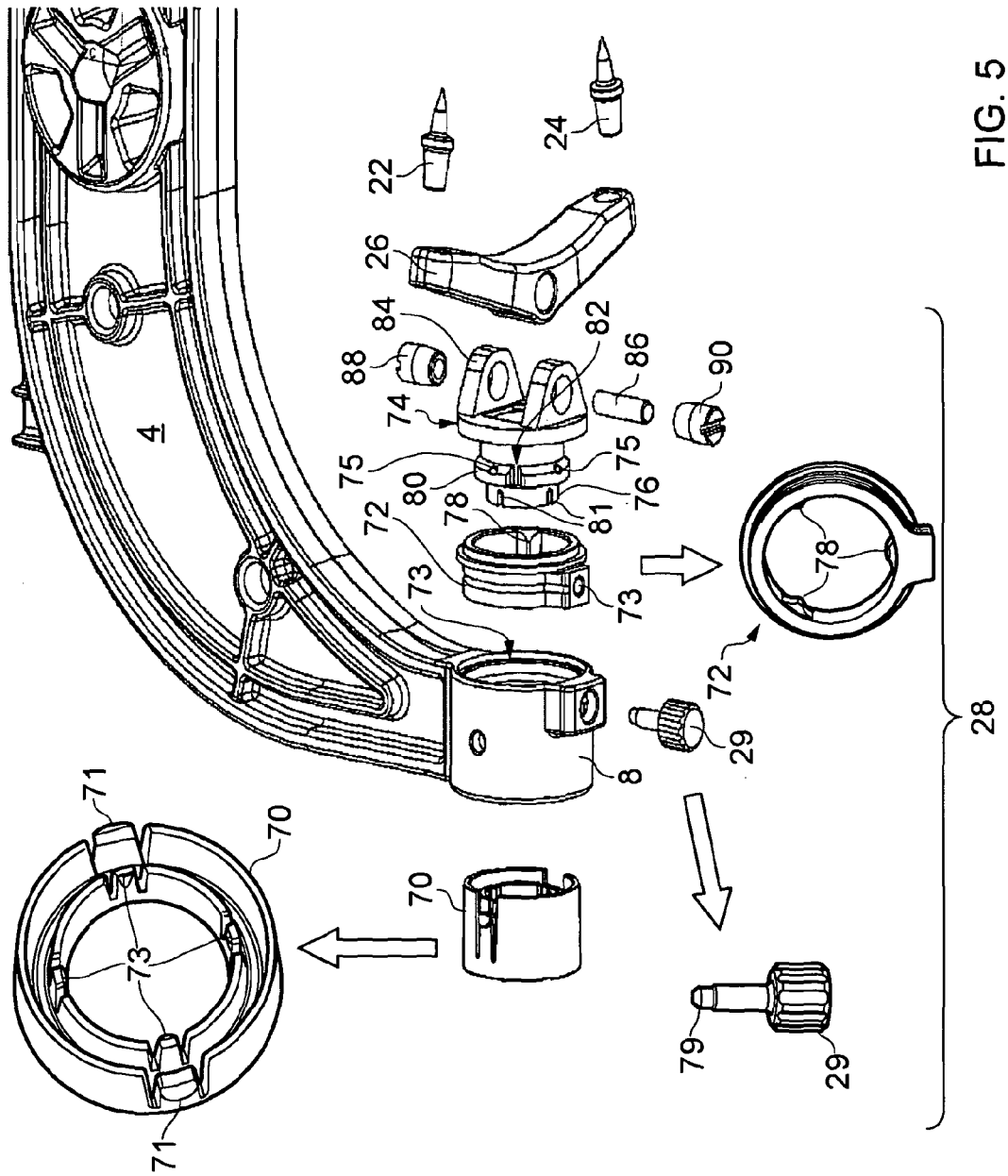
Figure 7:
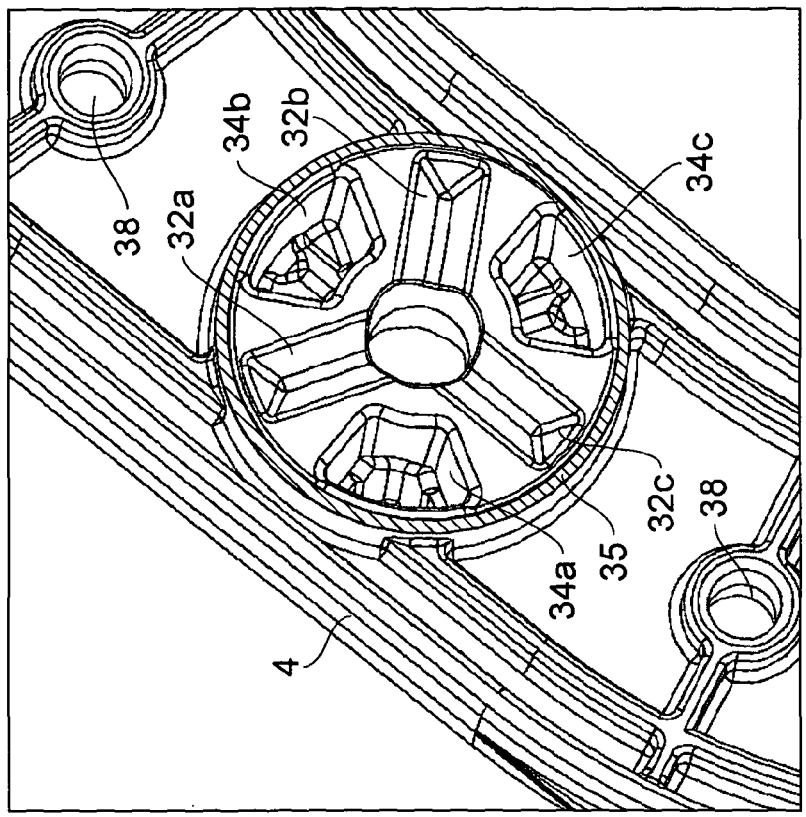
Figure 6:
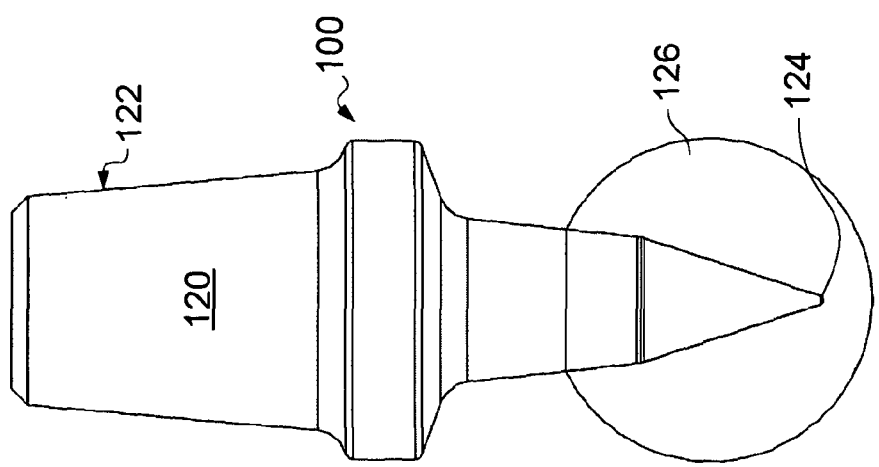
Figure 9:
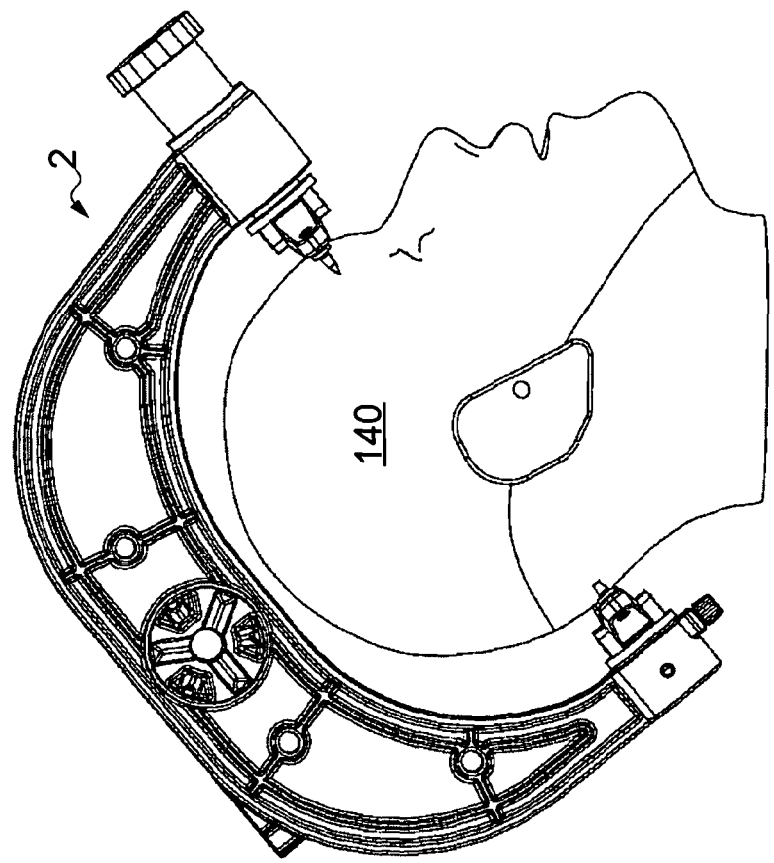
Figure 8:
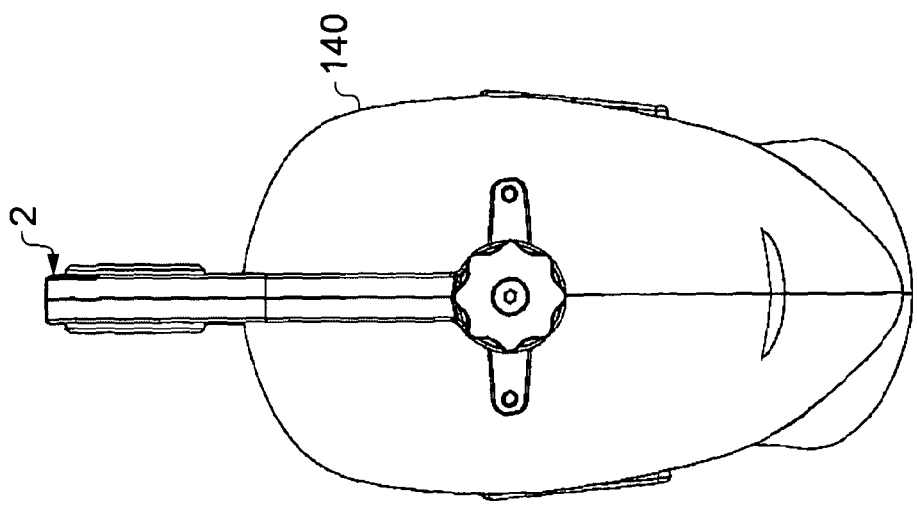
Figure 11:
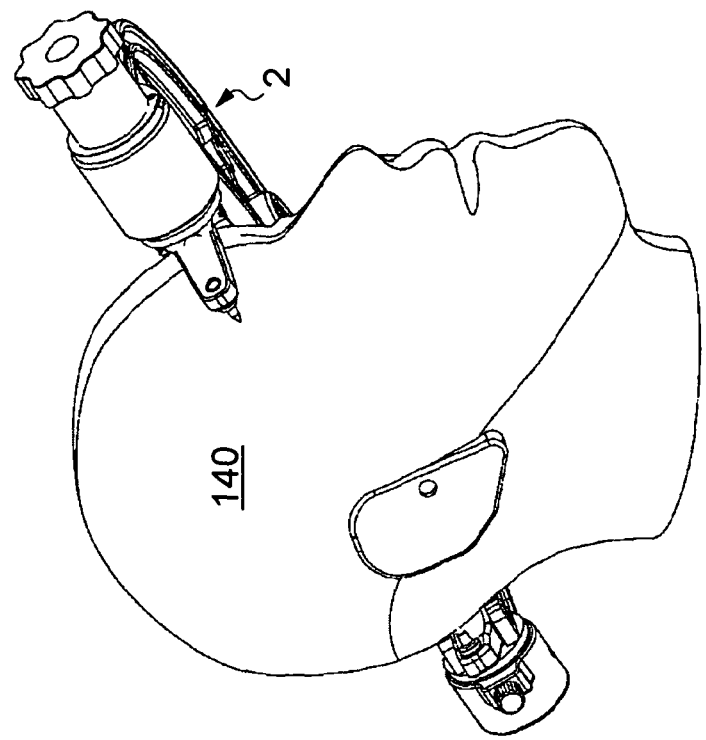
Figure 10:
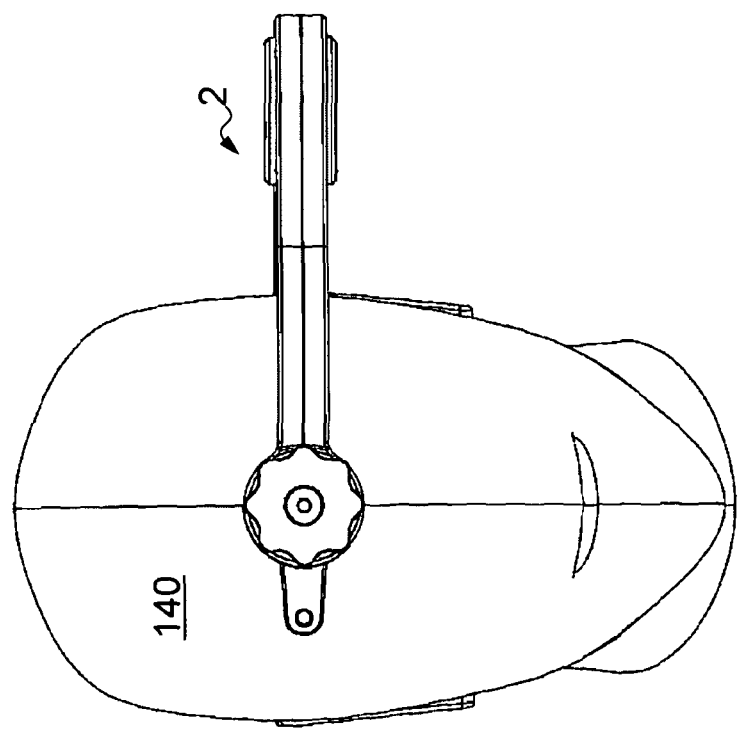
Figure 12:
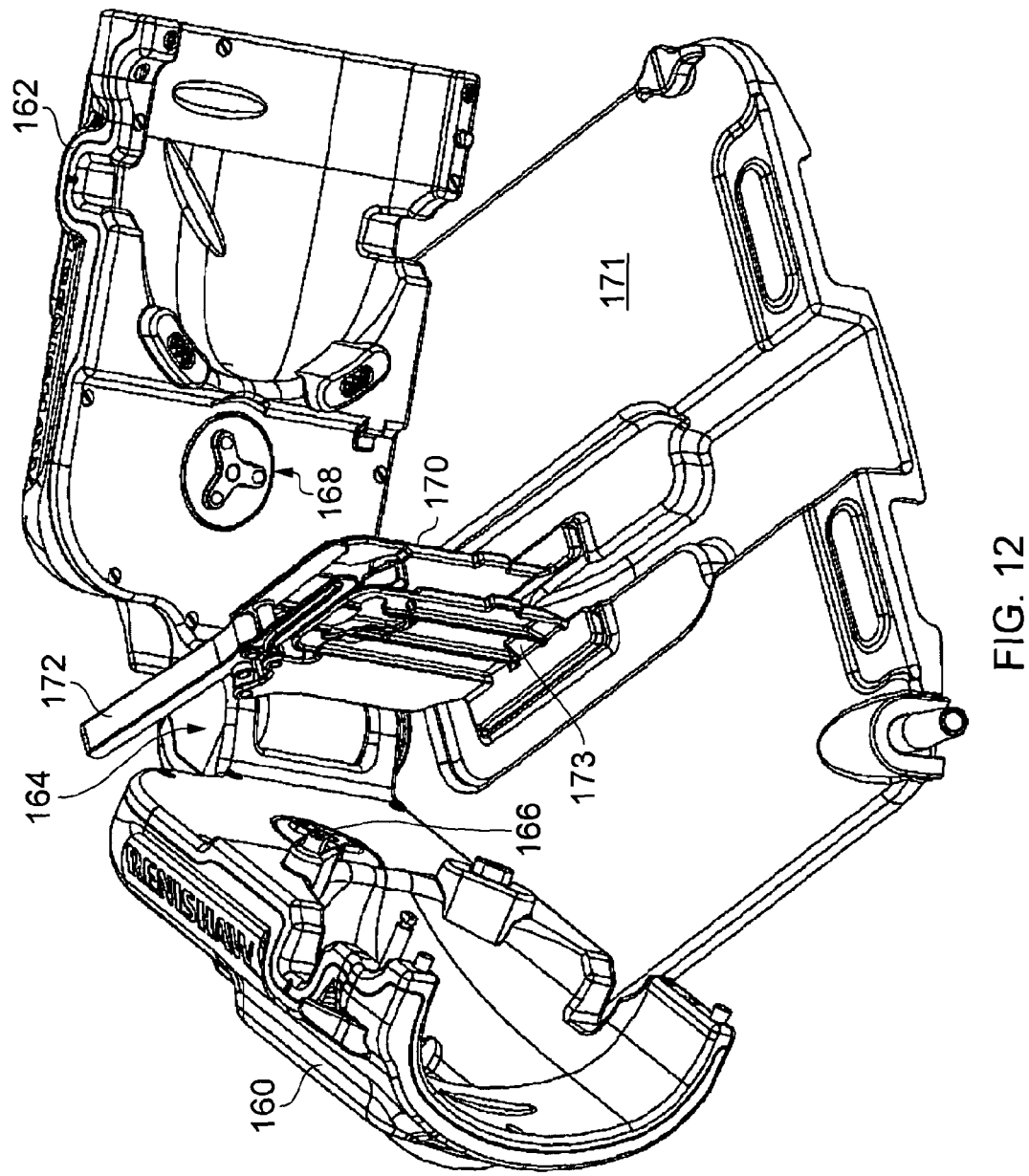
Figure 13:
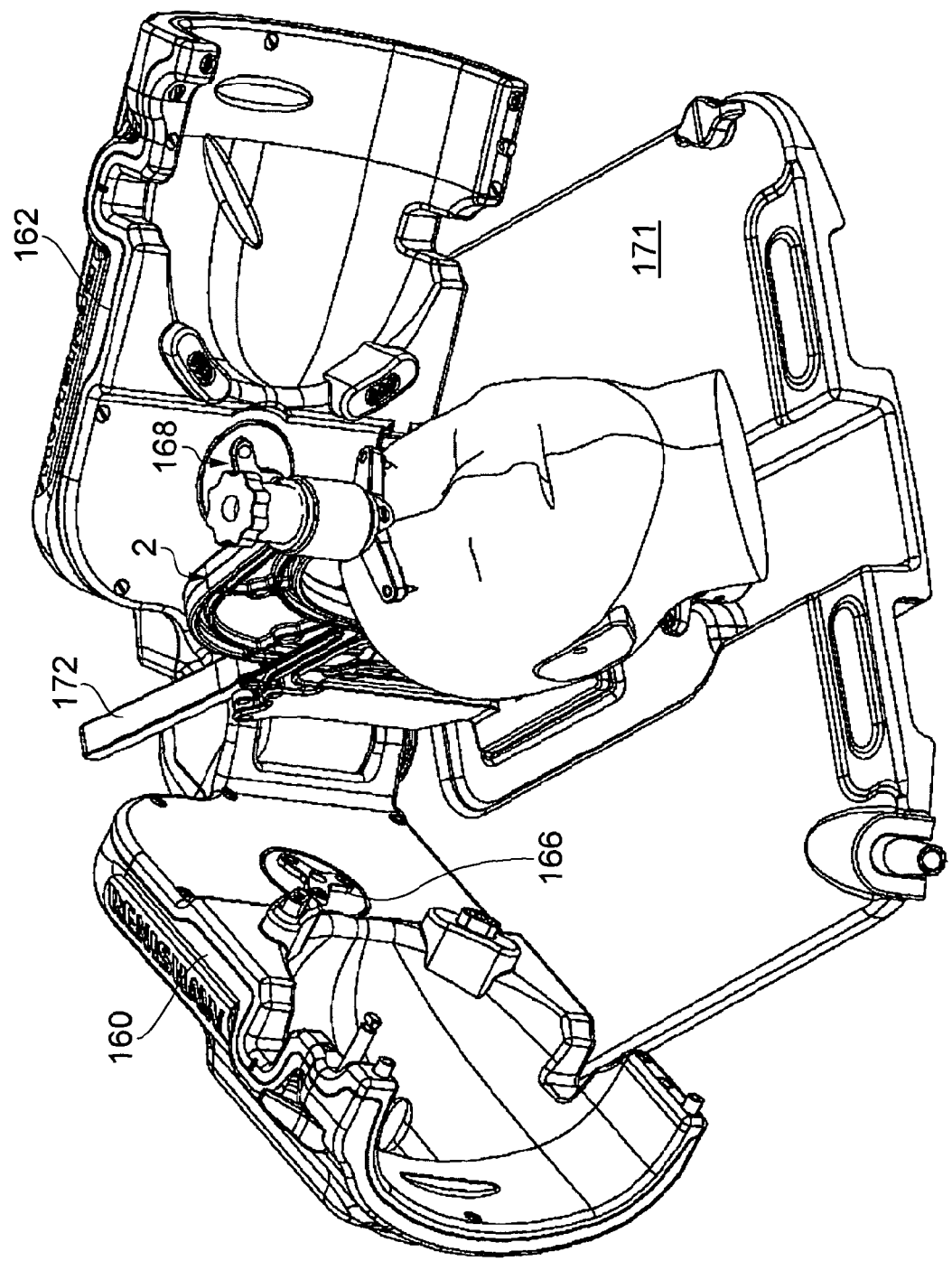
Figure 14:
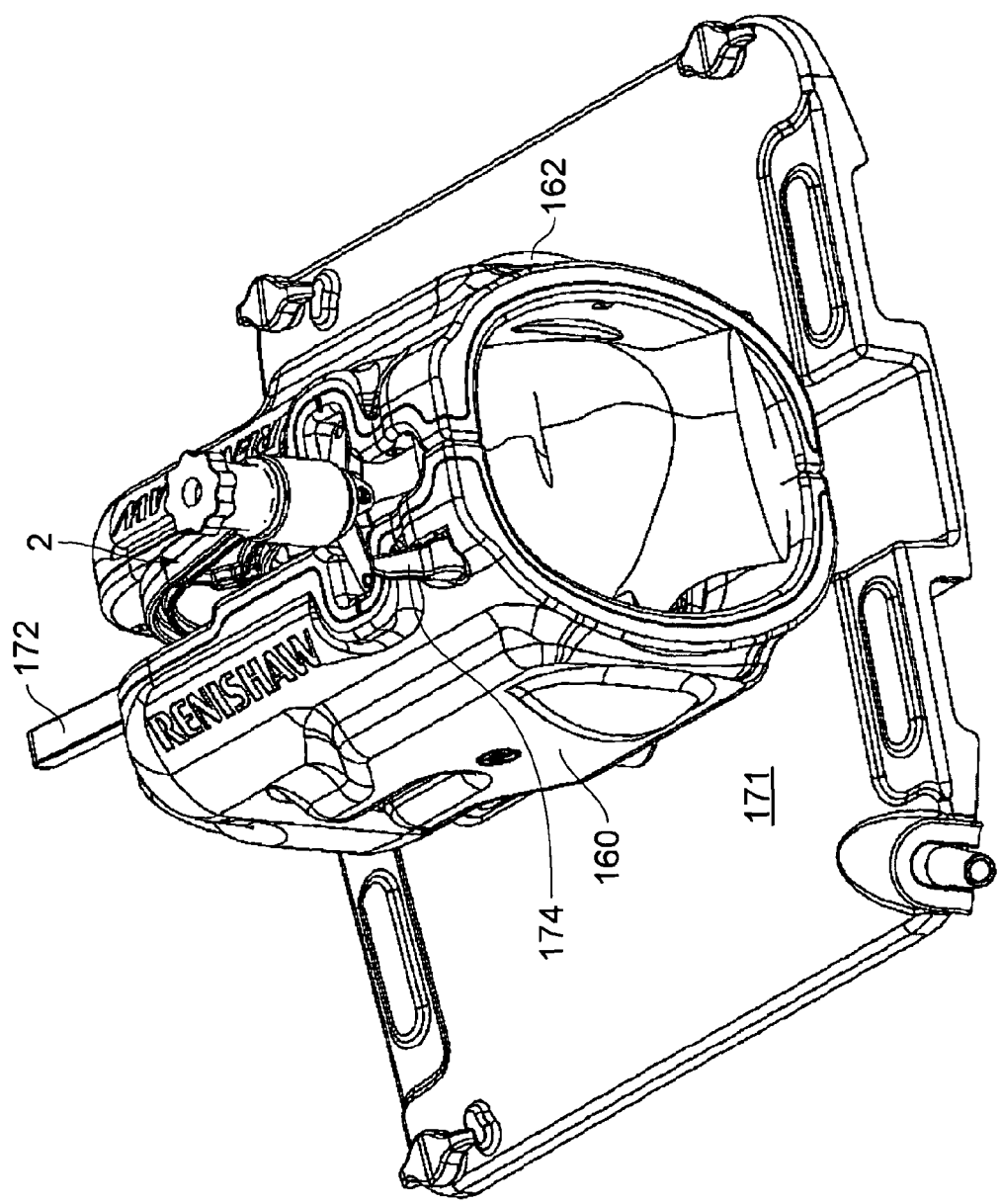
Figure 15:
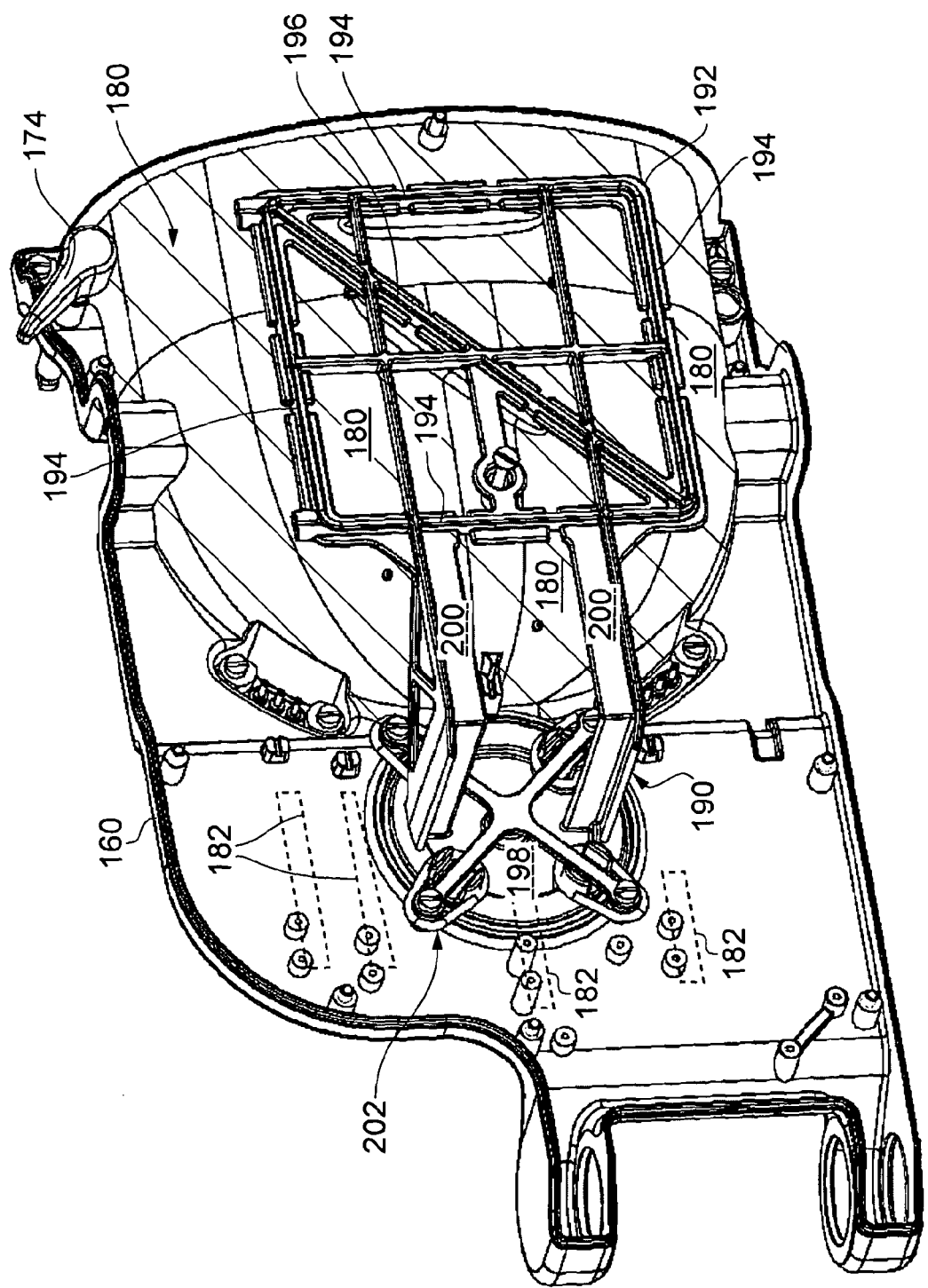
Figure 18:
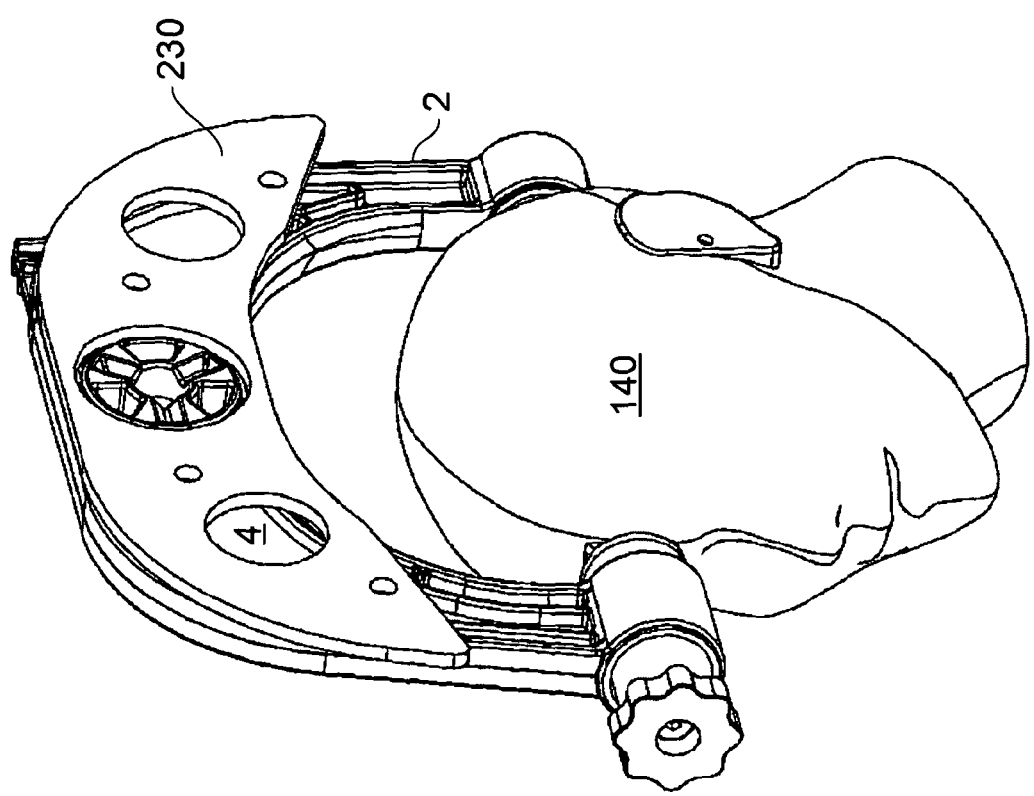
Figure 19:
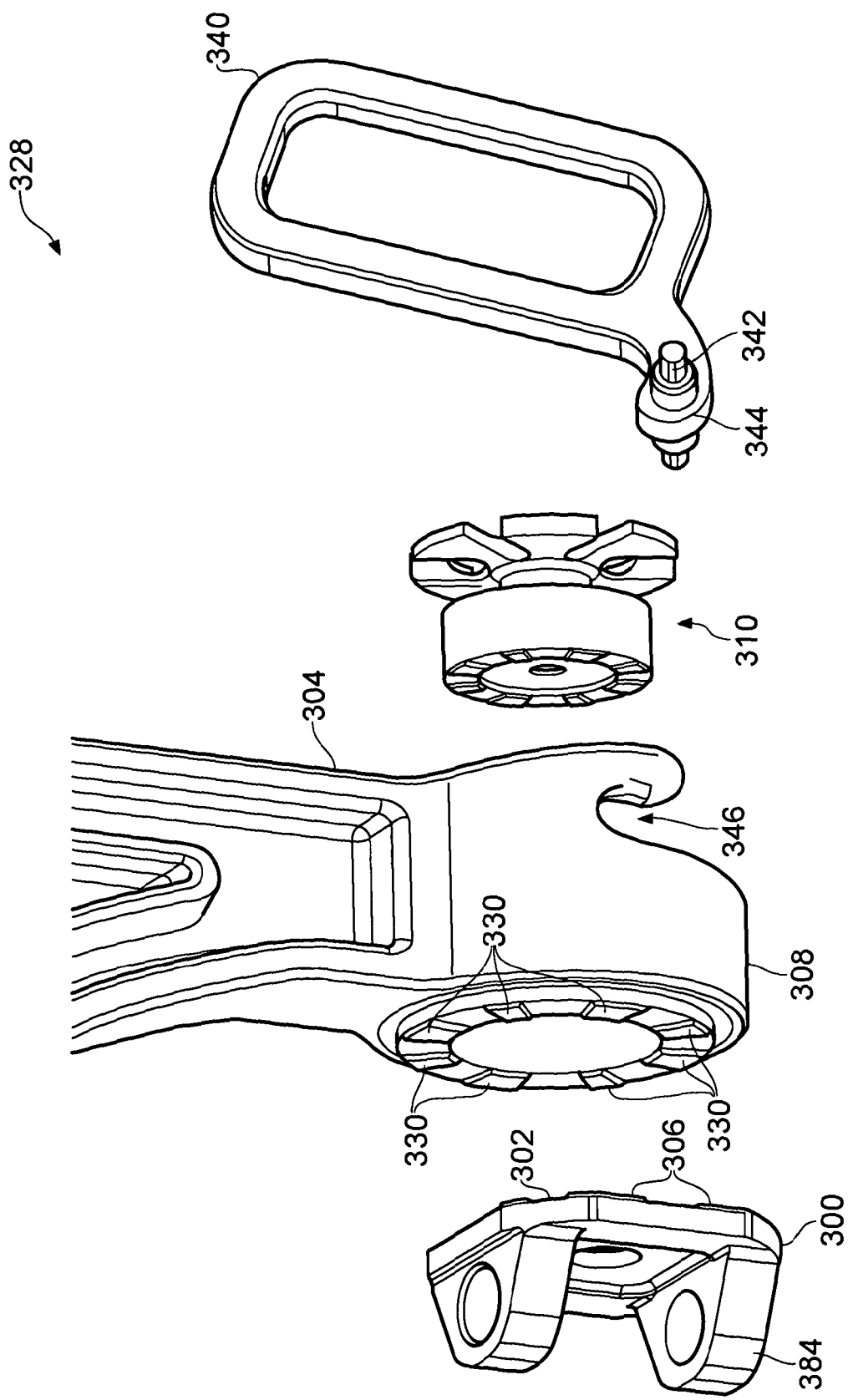
Figure 20:
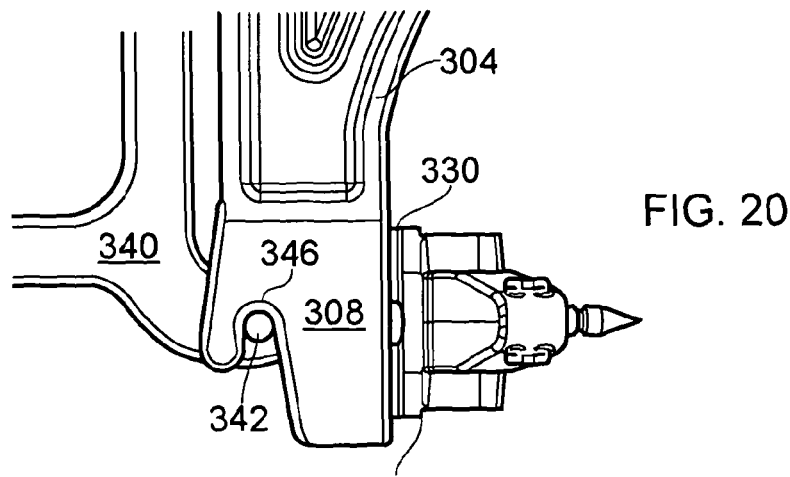
Figure 21:
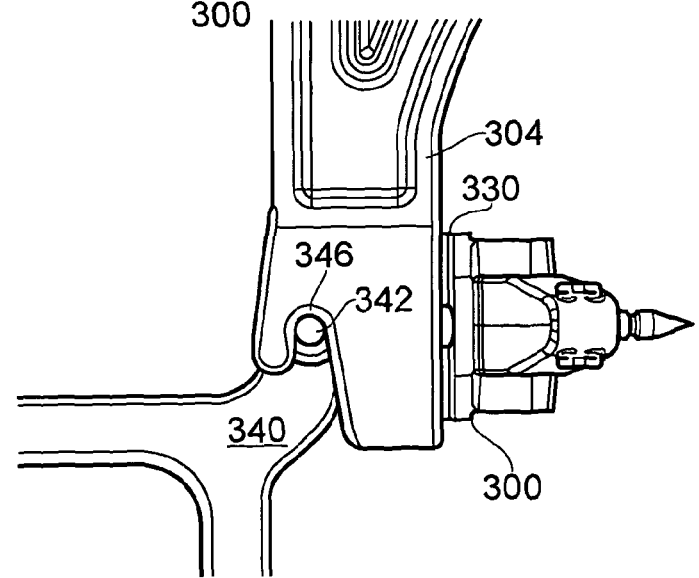
Figure 22:
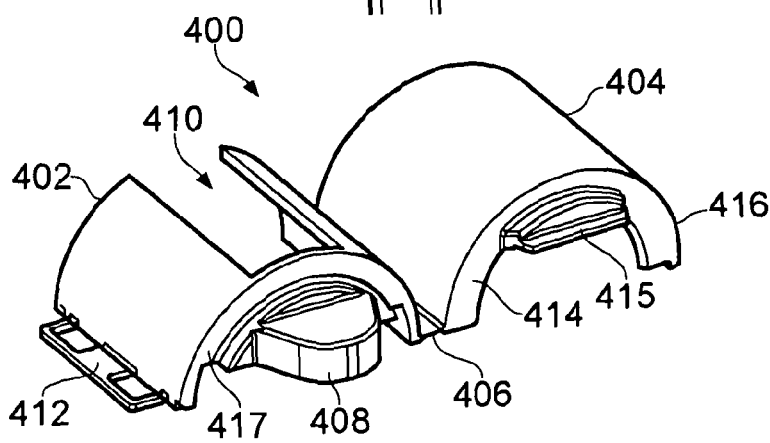
Figure 23:
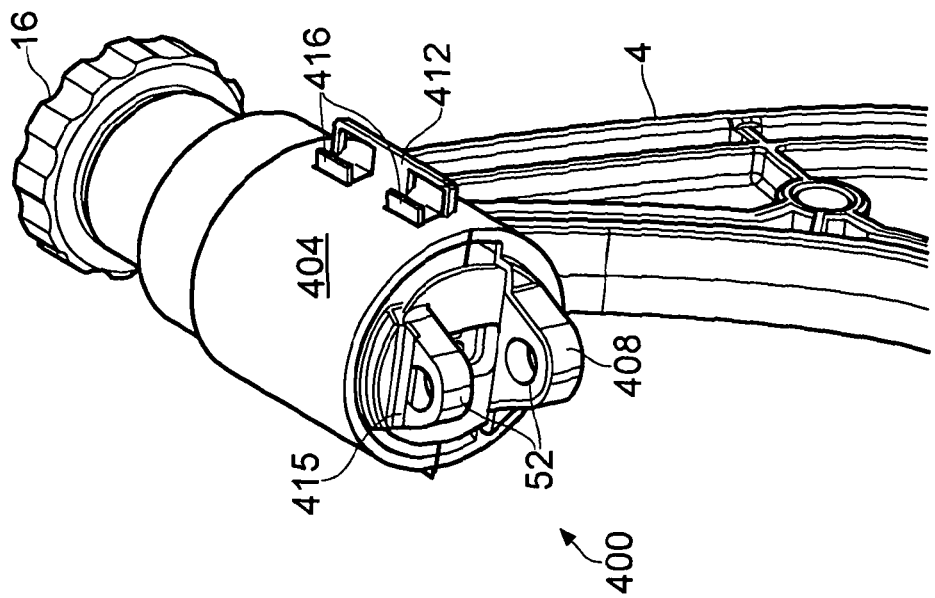
Figure 24:
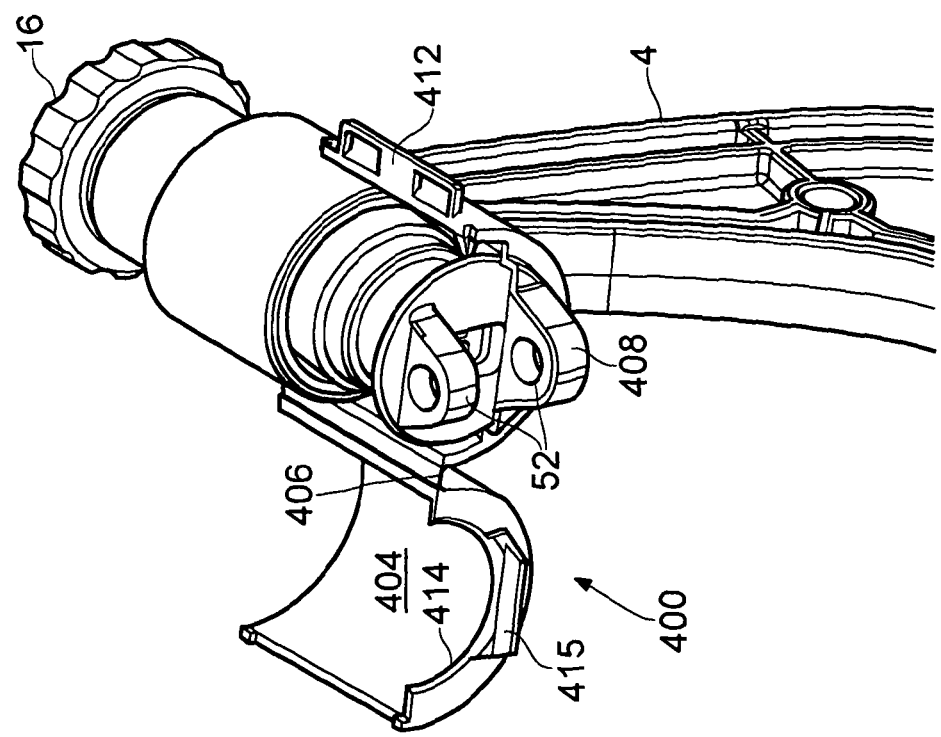

The invention will now be described, by way of example only, with reference to the accompanying drawings in which;

FIG. 1 illustrates a head clamp of the present invention,

FIG. 2 shows an exploded view of the force control mechanism of the head clamp of FIG. 1, FIG. 3 is a view of the force control mechanism prior to the required force being applied, FIG. 4 is a view of the force control mechanism when the required force is being applied, FIG. 5 is an exploded view of the indexing mechanism of the head clamp of FIG. 1, FIG. 6 illustrates a rubber coated attachment pin, FIG. 7 shows the kinematic datum feature of the head clamp in more detail, FIG. 8 shows a frontal view of the head clamp when attached to a head and indexed into a first (imaging) configuration, FIG. 9 shows a side view of the head clamp when attached to a head and indexed into a first (imaging) configuration, FIG. 10 shows a frontal view of the head clamp when attached to a head and indexed into a second (surgical) configuration, FIG. 11 shows a side view of the head clamp when attached to a head and indexed into a second (surgical) configuration, FIG. 12 shows MRI imaging apparatus for receiving a head clamp of the type shown in FIGS. 1 to 11 in an open configuration, FIG. 13 shows a head clamp retained by the MRI apparatus, FIG. 14 shows the MRI imaging apparatus in a closed configuration, FIG. 15 shows one part of the housing of the MRI imaging apparatus in more detail, FIG. 16 provides a more detailed view of how the fiducial marker assembly is attached to the housing, FIG. 17 provides an exploded view of how the fiducial marker assembly is attached to the housing, FIG. 18 shows an optional support or back-up clamp for the head clamp, FIG. 19 is an exploded view of a Hirth coupling that can provide an alternative indexing mechanism for the head clamp of FIG. 1, FIG. 20 shows the Hirth coupling of FIG. 19 in an unlocked configuration, FIG. 21 shows the Hirth coupling of FIG. 19 in a locked configuration, FIG. 22 shows an anti-rotation device for locking the force applicator mechanism of a head clamp as shown in FIG. 1, FIG. 23 shows the anti-rotation device of FIG. 22 in an open configuration when engaging the head clamp, and FIG. 24 shows the anti-rotation device of FIG. 22 in a closed configuration that prevents rotation of the force applicator mechanism.

Referring to FIG. 1, a head clamp 2 of the present invention is illustrated. The head clamp 2 comprises a generally c-shaped member 4 having a first end 6 and a second end 8.

At the first end 6 of the c-shaped member 4, a first pair of skull attachment pins 10 and 12 are mounted to a first v-shaped pin carrying member 14. The first v-shaped member 14 is pivotally connected at its apex to a force applicator mechanism 16 which is in turn attached to the first end 6 of the c-shaped member 4. The first v-shaped member 14 is pivotable about the axis P1 such that the pins 10 and 12 can rotate in a single plane. The force applicator mechanism 16 comprises a profiled portion 18 which can be rotated to drive the first v-shaped pin carrying member 14 along the clamping force axis 20 thereby allowing the head clamp to be secured to the head of a subject. More details of the force applicator mechanism 16 are outlined below with reference to FIG. 2.

At the second end 8 of the c-shaped member 4 there is provided a second pair of skull attachment pins 22 and 24 that are mounted to a second v-shaped pin carrying member 26. The second v-shaped member 26 is pivotally connected to an indexing mechanism 28 that is in turn mounted to an aperture provided at the second end 8 of the c-shaped member 4. The second v-shaped member 26 is pivotable about the axis P2 such that the pins 22 and 24 can rotate in a single plane. The indexing mechanism 28 comprises a locking screw 29 for locking the selected indexed position. More details of the indexing mechanism 28 are provided below with reference to FIG. 3.

The c-shaped member 4 is approximately mechanically symmetrical about the plane 30 which provides a neutral axis of distortion. A neutral axis of distortion is thus the axis of symmetry of the c-shaped member 4 that is not subject to compression or tension (i.e. is not distorted) when the head clamp exerts a clamping force on a head. The c-shaped member 4 also comprises ribs 31 to improve stiffness and in particular to reduce the possibility of the c-shaped member 4 twisting. In this example, the c-shaped member 4 is formed from a glass-filled polymer material, such as Ryton R7, which is light, stiff and MRI compatible. It should be noted that it would also be possible to use other materials (e.g. ceramic) to form the c-shaped member. For example, a number of different polymer materials could be used and it would also be possible to use a ferrous metal (such as steel) if MRI compatibility was not required.

On both faces of the c-shaped member 4 there are provided identical datum features that lie on a neutral axis. The datum feature shown in FIG. 1 comprises three sub-features in the form of v-grooves 32a-32c that are radially spaced apart from one another by 120° and extend along directions that intersect at a common point. As explained in more detail below, the v-grooves 32a-32c of the datum feature provide a repeatable, kinematic, mechanical link with associated apparatus such as a stereoguide or MRI fiducial marker assemblies. The c-shaped member 4 also comprises an attachment feature on each face. The attachment feature is, in this example, provided in the form of three recesses 34a-34c and a circular rim portion 35.

The three recesses 34a-34c and/or the circular rim portion 35 can be used to provide a pseudo-kinematic link that allows the head clamp to be secured to apparatus such as a surgical bed or MRI apparatus in an approximate position. In this example, attachment features are provided on both faces that are co-axial with the datum features and therefore also lie substantially on the neutral axis. It would, of course, also be possible to space apart the attachment and datum features and/or provide either feature on only one face. In this example, supplementary attachment features are also provided by the protrusion 37 and the apertures 38 provided in the c-shaped frame 4. Apparatus may be secured to the head clamp 2 using some or all of the attachment features and supplementary attachment features as appropriate; this is described in more detail below.

More details of the various parts of the head clamp of FIG. 1 will now be described with reference to FIGS. 2 to 7.

Referring to FIG. 2, the force applicator mechanism 16 is illustrated in an exploded view. The force applicator mechanism 16 comprises a force control member 40 that comprises the profiled portion 18 at its proximal end, a force indication rod 42, a helical spring 44, a hollow cylindrical sleeve 48 that fits within the aperture at the first end 6 of the c-shaped member 4 and a shaft portion 50. An optional clamping element 46 may also be provided to lock the force control member 40 to the first end 6 of the c-shaped member 4. The distal end of the shaft portion 50 comprises a yoke 52 to which the v-shaped pin carrying member 14 can be attached using a pair of pivot bolts 56 and 58 and a threaded loading stud 54. Skull attachment pins 10 and 12 can be attached to the tapered apertures of the v-shaped pin carrying member 14.

The force applicator mechanism 16, when assembled, allows a predetermined force to be applied to the skull via the skull attachment pins 10 and 12. In particular, rotation of the force control member 40 causes the spring 44 to urge the shaft portion 50 along the clamping axis 20 thereby moving the pins 10 and 12 into engagement with the skull. As the clamping force applied to the skull is increased, the spring 44 compresses which in turn causes the force indication rod 42 to move relative to the force control member 40. The face 60 of the force indication rod 42 become flush with the face 62 of the profiled portion 18 when the required, preset, clamping force is being applied. Although not shown, an optional force limiter may be provided to prevent the preset clamping force being exceeded.

Referring now to FIG. 3, the tactile indicator of the force applicator mechanism 16 is shown before the predetermined clamping force is applied. It can be seen that the face 60 of the force indication rod 42 is sub-flush or recessed with respect to the face 62 of the profiled portion 18 of the force control member 40.

Referring to FIG. 4, the tactile indicator of the force applicator mechanism 16 is shown when the required, predetermined, clamping force is applied. It can be seen that the face 60 of the force indication rod 42 is flush with respect to the face 62 of the profiled portion 18 of the force control member 40. This provides the user with a simple, tactile, indication that the desired clamping force is being applied.

Referring to FIG. 5, the indexing mechanism 28 is shown in an exploded view with insets providing alternative views of several components. The indexing mechanism comprises a detent insert 70, an indexer body ring 72, a locking or indexing screw 29 and an indexer-head shaft 74. The distal end of the indexer-head shaft 74 comprises a yoke 84 to which the v-shaped pin carrying member 26 can be attached using a pair of pivot bolts 88 and 90 and threaded loading stud 86. Skull attachment pins 22 and 24 can be attached to tapered apertures of the v-shaped pin carrying member 26.

The indexer-body ring 72, when assembled, is moulded into an indexer-eye 73 provided at the inwardly facing side of the aperture provided at the second end 8 of the c-shaped member 4. The proximal end 76 of the indexer-head shaft 74 can, when the locking screw 29 is unscrewed, freely rotate within the indexer body ring 72. The indexing mechanism is configured to operate when the head frame is clamped to the head and hence, in use, there will be a force of around 400 N urging the indexer-head shaft 74 into engagement with the indexer-body ring 72.

The locking screw 29 has a conical tip 79 and the indexer-head shaft 74 comprises a chamfered collar 80 in which are formed a plurality of conical depressions 75. The indexer-body ring 72 comprises three chamfered buttresses. The required indexed position is locked when the conical tip 79 of the indexer screw 29 emerges through the hole 73 in the indexer-body ring 72 and engages with one of the conical depressions 75 of the indexer-head shaft 74. When the screw 29 is fully engaged with a conical depression 75, the indexer-head shaft 74 is displaced fractionally away from its rotation axis so that its chamfered collar 80 is pushed into and supported by two chamfered buttresses 78 of the indexer-body ring 72. This three point support provides backlash free and accurate positioning.

The detent insert 70 is a moulded thermoplastic component that is held in place in the outwardly facing side of the aperture provided at the second end 8 of the c-shaped member 4 by a pair of sprung lugs 71. The purpose of the detent insert 70 is to guide the indexer-head shaft 74 into angular positions relative to the indexer-body ring 72 that are close enough to the locked or indexed positions to enable the indexer screw 29 to engage the selected one of the conical depressions 75. The detent insert 70 also forms the function of providing tactile feedback to a user that an indexed position has been achieved by clicking into place. The detent insert 70 comprises four protruding sprung elements 73 that provide this positional click by engaging with complementary slots 81 located at the index positions that are provided at the proximal end 76 of the indexer-head shaft 74.

The indexer-head shaft 74 is made in a single piece. This is not essential but has been found to aid positioning between the indexing components (e.g. the chamfered collar 80 and conical depressions 75) and the yoke 84 whilst also simplifying assembly and cleaning. Assembly of the indexer-head shaft 74 and the indexer-body ring 72 is made possible by the inclusion of slots 82 in the chamfered collar 80 which can be aligned with and pass over the chamfered buttresses 78.

The indexing mechanism 28 thus allows a plurality of discrete and repeatable indexed positions to be provided. It should, however, be noted alternative indexing mechanisms could be used to provide the same function. For example, the indexing mechanism may be implemented using a v-tooth (e.g. Curvic or Hirth) coupling, a plurality of pins that mate with a plurality of tapered holes or complementary sets of balls. Instead of the indexing mechanism of the present example, different types of position setter could be provided; for example, a rotary position encoder could be provided instead of the indexing mechanism.

Referring to FIG. 6, a pin 100 for engaging the skull of a subject is shown. Such a pin may be used in apparatus as described above or as part of any other appropriate surgical apparatus. The pin 100 comprises a titanium core having a tapered portion 122 (e.g. that can be pushed into the tapered bore on the arm of the v-shaped member) and a sharp skull engaging tip 124. Although a tapered connection between the pin and member is shown, other connections (e.g. threaded connections) may be provided. The skull engaging tip 124 is coated with a ball of a soft, e.g. rubber, material 126. This soft coating or material 126 helps prevent unwanted damage to soft tissue (e.g. skin) whilst a head clamp is being positioned but it can be readily pierced by the titanium tip when the pins are located in the required position and a clamping force is applied. It should be noted that the soft coating, although preferred, is by no means essential. Similarly, the pins may be formed from many materials other than titanium (e.g. other metals or ceramic etc). The pin 100 may be permanently attached to a part of the head clamp but it is preferably provided as disposable (e.g. single use) item that can be easily attached to and detached from the head clamp.

Referring to FIG. 7, the datum and attachment features of the head clamp are shown in more detail. The datum feature comprises three v-grooves 32a-32c that are radially spaced apart from one another by 120°. The attachment feature comprises three recesses 34a-34c and the circular rim portion 35. Apertures 38 that are provided as part of the supplementary attachment features are also shown.

A number of potential uses of the head clamp described with reference to FIGS. 1 to 7, along with methods of attaching the head clamp to a subject, will now be described with reference to FIGS. 8 to 11.

In use, the head clamp 2 is placed over a subject's head so that the c-shaped member 4 partially encircles the head. The pins 10 and 12 provided at the first end 6 of the c-shaped member 4 are aligned with the centre of the forehead and the pins 22 and 24 provided at the second end 8 of the c-shaped member 4 are located on the opposite side (rear) of the head. The clamping axis 20 of the head clamp is also approximately aligned with the cantho-meatal plane. An alignment aid, for example a band attached to the head or an alignment aid mounted to the head clamp, may be used to facilitate the required alignment. The first and second v-shaped members 14 and 26 are also respectively arranged such that the pins 10 and 12 pivot in substantially the same plane as the pins 22 and 24. Once aligned, the profiled portion 18 of the force applicator mechanism 16 is turned thereby advancing the pins 10 and 12 towards the head. The applied force is then increased until the pins 10, 12, 22 and 24 cut through the skin and engage the underlying skull bone with the required, predetermined, amount of force. In this example, a total force of 400 N is applied which results in each pin applying a 200 N force to the skull bone. Pivoting of the first and second v-shaped members 14 and 26 ensures that the force is evenly applied to the skull through each pin.

Applying a predetermined (preset) amount of force evenly distributed through the pins has the advantage that the c-shaped member 4 will deform by substantially the same amount each time it is attached to a head. Furthermore, locating the datum and attachment features substantially on the neutral axis ensures that the position of such features is substantially invariant even if the c-shaped member is subjected to slightly different distortion forces.

FIGS. 8 and 9 show the head clamp 2 attached to a head 140 and indexed into a first, imaging, position. In this first position, the c-shaped member extends around the top of the head 140. This position is particularly suited for imaging applications, such as MRI, because it allows MRI coils and/or fiducial markers to be placed in close proximity to both sides of the head without any interference from the c-shaped member 4.

FIGS. 10 and 11 shows the head clamp 2 attached to the head 140 and indexed into a second position in which the c-shaped member extends around the side of the head. This second position provides the access to the top of the head that a surgeon typically requires to perform stereotactic neurosurgery.

Although two different indexed positions are shown in FIGS. 8-11, it should be noted that the c-shaped member of the head clamp could be indexable between more positions. For example, the c-shaped member could also be indexable into a position on the other side of the head and/or into any one or more other (e.g. intermediate) indexed positions. It is, however, preferably to provide only a few index positions to ensure that there is no potential for confusion over the index position that has been set. Markings may also be provided, if required, to help indicate the indexed position that has been adopted.

The positional differences between the various indexed positions adopted by the head clamp are preferably known or measured. For example, the head clamp may be designed so that there is a predetermined positional change in the position of one or more datum features between each of the indexed positions. Alternatively, a calibration procedure may be performed prior to use (e.g. during manufacture of the head clamp) in which the position of the datum feature is measured for different indexed positions. The head clamp may thus be supplied with a set of coordinate transformations that provide such position mapping information.

It should be noted that the head clamp may be formed from the glass filled polymer material mentioned above or any other suitable alternative material(s). The various parts of the head clamp may be single use (disposable), multi-use or re-useable. If any part of the head clamp can be used more than once, it is preferred that such a part can be sterilised in an autoclave.

Referring now to FIGS. 12 to 17, there will be described apparatus for imaging the head of subject that is designed for use with a head clamp of the type described with reference to FIGS. 1 to 11. Although the apparatus may be used with any imaging technique, the following examples describe its use with MRI apparatus.

FIG. 12 illustrates head imaging apparatus suitable for use in MRI that is placed in its open position. The apparatus comprises a housing formed from a first housing part 160 that is connected to a second housing part 162 by a pivot joint 164. As will be described in more detail with reference to FIG. 14-16 below, each housing part comprises a hollow plastic shell that contains RF coil assemblies for MRI, various electronic control circuitry and a floating fiducial marker assembly. The fiducial marker assemblies of the first and second housing parts are retained in their respective housing parts and have inwardly facing datum features 166 and 168 that are externally accessible through an aperture formed in the housing. A clamp mechanism in the form of a toggle clamp 170 is provided on the base 171 of the apparatus between the two housing parts 160 and 162.

As illustrated in FIG. 13, the toggle clamp 170 is designed such that activation of lever 172 causes the clamp to engage and hold the circular rim portions 35 of the two attachment features provided on the opposed faces of the c-shaped member 4 of the head clamp 2 that is described above with reference to FIGS. 1 to 11. The head imaging apparatus also comprises a channel 173 having angled walls for engaging the protrusion 37 of the c-shaped member 4 to provide additional mechanical support. The toggle clamp 170 is also arranged such that, when engaging the circular rim portions 35 of the head clamp 2, the datum features of the head clamp 2 are still accessible. In particular, the datum features 166 and 168 of the fiducial marker assemblies are arranged such that they can be brought into contact with the complementary datum features of the head clamp when held by the toggle clamp 170.

FIG. 14 illustrates the apparatus described above with reference to FIGS. 12 and 13 in its closed position. A two-part locking latch 174 is provided to hold the housing parts together in the closed position. In this closed position, the datum features 166 and 168 of the fiducial marker assemblies are biased into engagement with the complementary datum features of the head clamp 2. The fiducial markers of the fiducial marker assemblies are thus accurately held in a known, repeatable, position relative to the datum features of the head clamp. These fiducial markers thus act as highly accurate and repeatable reference position markers in any acquired MRI images.

Referring to FIG. 15, the components located within the first housing part 160 of the apparatus described with reference to FIGS. 12 to 14 will be described. It should be noted that the second housing part 162 houses similar components and is therefore not shown.

The first housing part 160 comprises a plastic shell that holds the various sets of RF coils 180 that can be used in conjunction with MRI apparatus to obtain high resolution images of the head. These RF coils 180 are secured to the housing and connected to electronic control circuitry provided on circuit boards 182. The RF coils 180 and circuitry 182 typically handle electrical signals during use and the first housing part therefore also acts as an insulating shield that prevents patients and operators being exposed to the electrical voltages. Cables to and from the electrical circuitry 182 are routed via the pivot joint of the housing.

The first housing part 160 also contains a first floating fiducial marker assembly 190. The fiducial marker assembly 190 comprises a fiducial marker 192 in the form of a square frame 194 with a diagonal cross member 196. The fiducial marker 192 comprises or contains a material that is MRI visible, such as copper sulphate solution. The fiducial marker assembly 190 also comprises a circular datum portion 198 having a surface protruding through an aperture in the housing that provides the externally accessible datum feature 166. A rigid right angled framework section 200 is also provided to connect the datum feature 166 to the fiducial marker 192.

As will be explained in more detail below, the fiducial marker assembly 190 is retained within the housing part 160 but is free to move relative to that housing part (i.e. it can be said to be floating or substantially unconstrained). This prevents any distortions of the housing being passed to the fiducial marker assembly and also permits the datum feature of the fiducial marker assembly to always adopt the same position relative to the complementary datum feature of the head clamp even if the housing parts do not adopt repeatable relative positions. A biasing mechanism 202 is, however, provided to retain the fiducial marker assembly and to bias the datum feature of that assembly into engagement with the head clamp during use.

Referring to FIGS. 16 and 17, the biasing mechanism 202 of the first housing part 160 described above is shown in cut-away and exploded cut-away views respectively.

The biasing mechanism 202 comprises an x-shaped flexible member 204 having four legs with ends that are each secured to the housing part 160 by separate screws 206. The centre of the x-shaped flexible member 204 engages a spherical protrusion 208 provided at the centre of the circular datum portion 198 of the fiducial marker assembly 190; the spherical protrusion 208 thus provides a single point of contact with the substantially flat flexible member 204. The biasing mechanism 202 also comprises four flexible loops 210. Each loop 210 is captured between the housing part 160 and one of the legs of the x-shaped flexible member 204 and also engages a protruding feature 212 provided on the circular datum portion 198. The loops are held in slight tension and, because they are equally spaced around the circumference of the circular datum portion 198, they maintain the circular datum portion 198 in a substantially central position within the aperture of the housing. The flexibility of the loops 210 and x-shaped member 204 does, however, allow movement of the fiducial marker assembly in all 6 degrees of freedom when necessary so as to enable the datum feature 166 to adopt the necessary position relative to a complementary datum feature provided on a head clamp. It should also be noted that the biasing mechanism 202 provides the only mechanical connection between the housing and the fiducial marker assembly and consequently any distortions of the housing will not be transmitted to that assembly.

The head clamp and imaging apparatus described above are designed to be used together, but it is important to note that each could be used separately for different purposes. For example, the head clamp could be used purely for clamping a head during surgical or other procedures. Similarly, the imaging apparatus could be arranged to engage and image other body parts to which other fixtures are attached.

It should be remembered that the head clamp described above with reference to FIGS. 1 to 11 is also designed to be used in surgical procedures. In particular, once an MRI image of the head has been obtained, the head clamp may be indexed to at least one further position that is suitable for conducting a surgical procedure.

The, or each, datum feature provided on the head clamp may thus be used to locate other apparatus in a known position relative to the head clamp. For example, a datum feature could be used to accurately position, relative to the head clamp, retro-reflective surgical navigation instruments, surgical robots such as the Renishaw-Mayfield neuromate (Registered Trade mark) robot, and targeted radiotherapy devices such as the Leksell gamma-knife (Registered Trade mark) apparatus. Position information acquired from the MRI images can then be tied back to the datum feature on the head clamp and can therefore be used to precisely target regions or points in the brain.

Although the mechanical strength of the c-shaped member 4 of the above described head clamp is designed to be more than adequate for all expected mechanical loads to which it will be subjected in use, it is noted that the head clamp may, on very rare occasions, be subjected to large mechanical impulses that could exceed safe design limits. For example, a surgeon may have no choice other than subjecting the head clamp to large forces to perform an emergency procedure (e.g. resuscitation etc). In the case of a c-shaped member formed from a rigid material, such as a glass filled polymer, any failure may be catastrophic; this can obviously have severe consequences if a neurosurgical procedure is in progress.

Referring to FIG. 18, a supplementary support or backup clamp 230 (e.g. formed from metal) is shown that can be attached to the head clamp 2 during surgery. The backup clamp 230 may, for example, attach to the apertures 38 (not visible in FIG. 18 but shown in FIG. 1) formed in the c-shaped member 4 of the head clamp 2. The supplementary clamp 230 is arranged so that access to the datum feature of the head clamp 2 is maintained. In normal use, the supplementary clamp 230 takes none of the mechanical load of the head clamp 2 but it does, however, act as a backup device that takes the full mechanical load of the head clamp 2 if that head clamp 2 was to fail. The supplementary clamp 230, which is by no means essential, thus mitigates the unwanted consequences that might occur with a catastrophic failure of the head clamp 2.

Referring to FIG. 19, an exploded view is shown of an indexing mechanism 328 suitable for inclusion in a head clamp as described above. The indexing mechanism 328 may, for example, be provided instead of the indexing mechanism 28 described in detail with reference to FIG. 5.

The indexing mechanism 328 comprises a so-called Hirth coupling in which a series of concentric features 330 are provided around the aperture at the second end 308 of the c-shaped member 304. An indexable part 300 is also provided that has a face plate 302 comprising a plurality of concentric features 306 that complement the concentric features 330 of the c-shaped member 304. In particular, the complementary features 330 and 306 are configured such that, when biased into engagement, the indexable part 300 can adopt (i.e. can be indexed into) any one of multiple different orientations relative to the c-shaped member 304.

An indexing adjuster 310 and release lever 340 are also provided. The indexing adjuster 310 is insertable into the aperture at the second end 308 of the c-shaped member 304 and includes flexural elements to provide a preload bias (i.e. to bias the complementary features 330 and 306 into engagement even when the head clamp is not loaded) and stops to prevent the part being overloaded. The associated release lever 340 comprises a cam 344 and an axle 342. The axle 342 can be attached (clipped into) corresponding slots 346 provided at the second end 308 of the c-shaped member 304.

Rotation of the release lever 340, when the axle 342 is clipped into the slots 346, allows the cam 344 to engage and disengage the back surface of the indexing adjuster 310. Rotation of the release lever 340 can thus be used to force the cam 344 against the back surface, of the indexing adjuster 310 to separate the complementary features 330 and 306. Once these features are separated, the indexable part 300 can be indexed into a different orientation and locked in that orientation by rotating the release lever 340 to reduce the force applied by the cam 344. In other words, the indexing adjuster 310 and release lever 340 allow a user to axially separate the complementary features 330 and 306 to enable the indexable part 300 to be rotated into a different orientation relative to the second end 308 of the c-shaped member 304.

The indexable part 300 also comprises a yoke 384 to which a v-shaped pin carrying member (not shown in FIG. 19 but included in FIGS. 20 and 21 below) can be pivotally mounted in a similar manner to that described above with reference to FIG. 5.

Referring next to FIG. 20, the indexing mechanism 328 of FIG. 19 is shown when assembled. FIG. 20 shows the release lever 340 in the vertical or unlocked orientation in which the cam 344 and indexing adjuster 310 (not visible in FIG. 20) have forced the indexable part 300 out of engagement with the features 330 provided at the second end 308 of the c-shaped member 304. In this unlocked configuration, the c-shaped member 304 may be indexed into the required position.

Referring to FIG. 21, the indexing mechanism 328 of FIG. 19 is again shown when assembled but with the release lever 340 in the horizontal or locked orientation in which its cam 344 (not visible in FIG. 21) does not apply a disengaging force via the indexing adjuster 310 (also not visible in FIG. 21). The features of the indexable part 300 thus engage the features 330 provided at the second end 308 of the c-shaped member 304. In this locked configuration, the c-shaped member 304 is securely held in the required indexed position.

A Hirth coupling of this type has the advantage of providing accurate metrology whilst allowing multiple, repeatable, angular orientations to be selected. In particular, the arrangement does not necessarily require a separate locking piece because of the angle-defining features 330 and 306 provided at the second end 308 of the c-shaped member 304 and the face plate 302 respectively. These angle-defining features may, for example, be formed (e.g. ground) in the frame and/or face plate or may be formed in a component that is subsequently over-moulded into the end of the frame or into the face plate. The Hirth coupling offers low levels of backlash and self-centres. A further benefit of the Hirth coupling is that it is self-locking and resistant to accidental release when under load; the dimensions of the interlocking elements are also selected such that the mechanism can only engage in the allowed orientations (e.g. 0° and ±90°). Preferably, all of the components of the indexing mechanism 328 are MRI benign.

A head clamp of the type described above comprises a c-shaped, member having an indexing mechanism at one end and a force applicator mechanism at the other end. Each of these mechanisms preferably carry one or more pins for engaging the skull of a subject. Although these pins may be coated with a soft material, they can still present a sharps risk to the patient when the head clamp is being attached or removed.

The indexing mechanism of the head clamp is preferably lockable in various indexed positions when not loaded (i.e. when not attached to the skull of a subject). The various skull attachment pins carried by the indexing mechanism are thus prevented from rotating about the clamping axis when the head clamp is being attached or removed. In contrast, the pins carried by the force applicator mechanism are typically free to rotate about the clamping axis until they engage the skull. This free rotation can, in some instances, pose a sharps risk to the patient who may have their forehead scored from a rotating yoke and associated skull mounting pins during fitting or removal of the head clamp.

Referring to FIGS. 22 to 24, a yoke hold or anti-rotation device 400 is illustrated for reducing the risk of skin injury resulting from the free rotation of skull attachment pins that may be permitted by the force applicator mechanism.

FIG. 22 shows the anti-rotation device 400 in an open configuration. The anti-rotation device 400 comprises a first portion 402 linked to a second portion 404 by a hinge 406. The first and second portions 402 and 404 have a generally half cylindrical shape. The first portion 402 comprises a cradle grab 408, a slot 410, a clasp 412 and a circumferential boss 417. The second portion 404 comprises a circumferential boss 414, a protrusion 415 and a pair of ledges 416 (only partially visible in FIG. 20) that can mate with the clasp 412 of the first portion. The anti-rotation device 400 may be formed as a single piece from, for example, a suitable polymer. The anti-rotation device 400 may be a single use item or a multi-use item that is suitable for sterilisation.

As shown in FIGS. 23 and 24, the anti-rotation device 400 shown in FIG. 22 may be attached to the force applicator mechanism 16 described above with reference to FIGS. 1 to 4.

FIG. 23 shows the anti-rotation device 400 in its open configuration with the first portion 402 placed into contact with the force applicator mechanism 16.

FIG. 24 shows the anti-rotation device 400 after it has been closed around the force applicator mechanism 16. The pair of ledges 416 and clasp 412 cooperate to provide a snap fit lock that retains the anti-rotation device 400 in position. The slot 410 receives the c-shaped member 4 and prevents rotation of the anti-rotation device 400 relative to that c-shaped member 4. The cradle grab 408 and protrusion 415 of the anti-rotation device 400 engage the yoke 52 of the force applicator mechanism 16 and prevent it from rotating. In this manner, the yoke 52 is locked in a single orientation relative to the c-shaped member 4.

It should be noted that the anti-rotation device 400 can travel back and forth along the clamping axis with the yoke 52. In other words, the anti-rotation device 400 does not interfere with the normal operation of the force applicator mechanism 16 (i.e. which drives the yoke 52 back and forth). The anti-rotation device 400 can thus be used when attaching and/or detaching the head clamp to a subject. Removal of the anti-rotation device 400 (e.g. by unclipping it) when the head clamp is secured to a subject permits the c-shaped member to be indexed into the required orientation(s). In this manner, the anti-rotation device 400 reduces the sharps risk associated with using the head clamp without an adverse effect on its function.

It should be noted that the anti-rotation device 400 is by no means essential for operation of the head clamp. It should also be noted that alternative means for preventing rotation of the yoke carrying the skull attachment pins may be provided. For example, the force applicator mechanism 16 may comprise an integral anti-rotation component. Although the anti-rotation device 400 is described for use with the force applicator mechanism 16, the skilled person would also appreciate a similar device may be used to prevent any unwanted rotation of other force applicator mechanisms and/or the indexing mechanism. For example, a similar anti-rotation device may be used for alternative indexing mechanisms that have a freely rotatable yoke prior to engagement of the head clamp with the skull.

It should again be noted that the above embodiments are merely examples of the present invention. The skilled person would be aware of the many variations and alternative embodiments that would be possible.

The invention claimed is:

1. A head clamp for neurosurgery, comprising:
a member configured to at least partially encircle the head of a subject;
at least first and second skull attachment portions configured to attach the member to the head of the subject; and
an indexing mechanism that allows the member to be indexed between at least two repeatable relative positions when the head clamp is attached to the head of the subject, the at least two repeatable relative positions having a known position relative to each other,
wherein the indexing mechanism is configured to provide tactile feedback to a user to differentiate the at least two repeatable relative positions from other positions of the member when the head clamp is attached to the head of the subject.

2. A head clamp according to claim 1, wherein the member can, when attached to the head of the subject, be moved into a first position in which the member substantially extends around the top of the head to allow imaging of the head.

3. A head clamp according to claim 2, wherein the member can, when attached to the head of the subject, be moved into a second position in which the member substantially extends around a side of the head to enable neurosurgical procedures to be performed thereon.

4. A head clamp according to claim 1, wherein the indexing mechanism allows the member to be indexed between no more than ten repeatable relative positions.

5. A head clamp according to claim 4, wherein the indexing mechanism comprises a pair of mating parts.

6. A head clamp according to claim 1, wherein
the member comprises a c-shaped member, and
the first and second skull attachment portions are provided at first and second ends of the c-shaped member.

7. A head clamp according to claim 1, wherein
the first and second skull attachment portions are locatable on opposite sides of the head of the subject and can exert a clamping force on the head substantially along a clamping axis, and
the member is rotatable about the clamping axis.

8. A head clamp according to claim 1, wherein the first and second skull attachment portions each include two pins configured to directly engage the skull bone of the subject.

9. A head clamp according to claim 1, wherein the first and second skull attachment portions each comprise a pin carrying member that is pivotally attached to the member.

10. A head clamp according to claim 1, further comprising a force applicator configured to urge the first and second skull attachment portions into engagement with the skull with a predetermined force.

11. A head clamp according to claim 1, wherein the member comprises at least one datum feature, the at least one datum feature being located substantially on a neutral axis of distortion of the member.

12. A head clamp according to claim 1, further comprising at least one attachment feature that allows the head clamp to be secured to an associated apparatus, wherein the at least one attachment feature is located substantially on a neutral axis of distortion of the member.

13. A head clamp according to claim 1 that is MRI compatible.

14. A head clamping kit comprising:
a head clamp according to claim 1; and
a secondary clamping device attachable to the head clamp,
wherein the secondary clamping device provides, when attached to the head clamp, additional mechanical support to the member in the event of mechanical failure of that member.

15. An apparatus for imaging the head of a subject, comprising:
a head clamp according to claim 1; and
an apparatus configured to image a head, wherein the head clamp is releasably attachable to the apparatus configured to image the head.

16. An apparatus for neurosurgery, comprising:
a head clamp according to claim 1; and
a stereoguide device configured to retain and guide neurosurgical instruments,
wherein the stereoguide device is releasably attachable to the head clamp.

* * * * *